US009458191B2

(12) United States Patent
Chromy et al.

(10) Patent No.: US 9,458,191 B2
(45) Date of Patent: Oct. 4, 2016

(54) NANOLIPOPROTEIN PARTICLES AND RELATED METHODS AND SYSTEMS FOR PROTEIN CAPTURE, SOLUBILIZATION, AND/OR PURIFICATION

(71) Applicant: LAWRENCE LIVERMORE NATIONAL SECURITY, LLC, Livermore, CA (US)

(72) Inventors: Brett A. Chromy, Danville, CA (US); Paul Henderson, Dublin, CA (US); Paul D. Hoeprich, Jr., Pleasanton, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 77 days.

(21) Appl. No.: 14/536,513

(22) Filed: Nov. 7, 2014

(65) Prior Publication Data

US 2015/0105538 A1 Apr. 16, 2015

Related U.S. Application Data

(63) Continuation of application No. 12/352,548, filed on Jan. 12, 2009, now Pat. No. 8,907,061.

(60) Provisional application No. 61/020,638, filed on Jan. 11, 2008, provisional application No. 61/115,446, filed on Nov. 17, 2008.

(51) Int. Cl.
*C07K 1/14* (2006.01)
*C12N 11/02* (2006.01)
*C12P 3/00* (2006.01)

(52) U.S. Cl.
CPC .............. *C07K 1/145* (2013.01); *C12N 11/02* (2013.01); *C12P 3/00* (2013.01); *Y10S 977/799* (2013.01)

(58) Field of Classification Search
None
See application file for complete search history.

(56) References Cited

U.S. PATENT DOCUMENTS

| 4,317,771 | A | 3/1982 | Shiba et al. |
| 5,393,530 | A | 2/1995 | Schneider et al. |
| 7,015,471 | B2 | 3/2006 | Brewer et al. |
| 7,048,949 | B2 | 5/2006 | Sligar et al. |
| 7,083,958 | B2 | 8/2006 | Sligar et al. |
| 7,375,234 | B2 | 5/2008 | Sharpless et al. |
| 8,183,010 | B2 | 5/2012 | Swartz et al. |
| 2004/0180369 | A1 | 9/2004 | Franzen et al. |
| 2005/0244414 | A1 | 11/2005 | Mundy et al. |
| 2006/0189554 | A1 | 8/2006 | Mumper et al. |
| 2006/0211092 | A1 | 9/2006 | Sligar et al. |
| 2007/0117179 | A1 | 5/2007 | Kudlicki et al. |
| 2008/0124350 | A1 | 5/2008 | Mumper et al. |
| 2009/0192299 | A1 | 7/2009 | Chromy et al. |
| 2009/0311276 | A1 | 12/2009 | Hoeprich et al. |
| 2010/0203609 | A1 | 8/2010 | Yacoby et al. |

FOREIGN PATENT DOCUMENTS

| WO | 00/65099 | 11/2000 |
| WO | 02/40501 | 5/2002 |
| WO | 2004/094651 | 11/2004 |
| WO | 2005/070400 | 8/2005 |
| WO | 2006/073419 | 7/2006 |
| WO | 2007/038755 | 4/2007 |
| WO | 2007/050501 | 5/2007 |
| WO | 2008/028206 | 3/2008 |
| WO | 2008/106660 | 9/2008 |
| WO | 2009/100201 | 8/2009 |

OTHER PUBLICATIONS

Sun et al. "Overview of Protein Structural and Functional Folds", Current Protocols in Protein Science 2004, vol. 35, pp. 17.1.58-17.1.59.
Lee et al. "Ab Initio Protein Structure Prediction", in From Protein Structure to Function with Bioinformatics, © Springer Science + Business Media B.V. 2009, pp. 3-25.
Aranyi et al. "Predictable difficulty or difficulty to predict", Protein Science vol. 20 (2011), pp. 1-3.
Schmitt, L. et al. "Synthesis and Characterization of Chelator-Lipids for Reversible Immobilization of Engineered Proteins at Self-Assembled Lipid Interfaces" *J. Am. Chem. Soc.* 1994, 116, pp. 8485-8491.
Moses et al. "Detection of DNA hybridization on indium tin oxide surfaces" Sensors and Actuators B, 125 (2007) 574-580.
Bao et al. "High-Sensitivity Detection of DNA Hybridization on Microarrays Using Resonance Light Scattering" Anal. Chem (2002) 74:1792-1797.
Brown et al. "Exploring the new world o the genome with DNA microarrays" Nature Genetics, (1999) 21:33-37.
Brewer et al. "Formation of Thiolate and Phosphonate Adlayers on Indium-Tin Oxide: Optical and Electronic Characterization" Langmuir (2002) 6857-6865.
Advisory Action mailed on Jun. 6, 2012 for U.S. Appl. No. 12/118,530, filed May 9, 2008 in the name of Matthew A. Coleman. 5 pages.
Non-Final Office Action mailed on Jul. 24, 2014 for U.S. Appl. No. 12/118,530, filed May 9, 2008 in the name of Matthew A. Coleman. 33 pages.
Final Office Action mailed on Mar. 6, 2015 for U.S. Appl. No. 12/118,530, filed May 9, 2008 in the name of Matthew A. Coleman. 52 pages.

(Continued)

Primary Examiner — Anand Desai
(74) Attorney, Agent, or Firm — Steinfl & Bruno LLP

(57) ABSTRACT

Provided herein are methods and systems for assembling, solubilizing and/or purifying a membrane associated protein in a nanolipoprotein particle, which comprise a temperature transition cycle performed in presence of a detergent, wherein during the temperature transition cycle the nanolipoprotein components are brought to a temperature above and below the gel to liquid crystalling transition temperature of the membrane forming lipid of the nanolipoprotein particle.

9 Claims, 35 Drawing Sheets

(56) References Cited

OTHER PUBLICATIONS

Advisory Action mailed on Jun. 7, 2012 for U.S. Appl. No. 12/118,396, filed May 9, 2008 in the name of Matthew A. Coleman. 5 pages.
Non-Final Office Action mailed on Jul. 22, 2014 for U.S. Appl. No. 12/118,396, filed May 9, 2008 23 in the name of Matthew A. Coleman. 28 pages.
Final Office Action mailed on Feb. 4, 2015 for U.S. Appl. No. 12/118,396, filed May 9, 2008 in the name of Matthew A. Coleman. 29 pages.
Advisory Action mailed on Jul. 7, 2015 for U.S. Appl. No. 12/118,396, filed May 9, 2008 in the name of Matthew A. Coleman. 8 pages.
Restriction Requirement mailed on Jun. 7, 2011 for U.S. Appl. No. 12/469,533, filed May 20, 2009 in the name of Paul D. Hoeprich. 8 pages.
Final Office Action mailed on Oct. 24, 2011 for U.S. Appl. No. 12/469,533, filed May 20, 2009 in the name of Paul D. Hoeprich. 11 pages.
Non-Final Office Action mailed on May 23, 2012 for U.S. Appl. No. 12/469,533, filed May 20, 2009 in the name of Paul D. Hoeprich. 15 pages.
Final Office Action mailed on Dec. 4, 2012 for U.S. Appl. No. 12/469,533, filed May 20, 2009 in the name of Paul D. Hoeprich. 7 pages.
Notice of Allowance mailed on Jul. 3, 2014 for U.S. Appl. No. 12/469,533, filed May 20, 2009 in the name of Paul D. Hoeprich. 30 pages.
Non-Final Office Action mailed on Oct. 2, 2013 for U.S. Appl. No. 12/352,472, filed Jan. 12, 2009 in the name of Sarah E. Baker. 19 pages.
Non-Final Office Action mailed on Dec. 26, 2014 for U.S. Appl. No. 12/352,472, filed Jan. 12, 2009 in the name of Sarah E. Baker. 24 pages.
Final Office Action mailed on Jun. 29, 2015 for U.S. Appl. No. 12/352,472, filed Jan. 12, 2009 in the name of Sarah E. Baker. 18 pages.
PCT Written Opinion for PCT/US2009/033193 filed on May 2, 2009 on behalf of Lawrence Livermore National Security, LLC mail date: Sep. 30, 2009. 7 pages.
PCT International Search Report for PCT/US2009/033193 filed on May 2, 2009 on behalf of Lawrence Livermore National Security, LLC mail date: Sep. 30, 2009. 4 pages.
PCT International Preliminary Report on Patentability for PCT/US2009/033193 filed on May 2, 2009 on behalf of Lawrence Livermore National Security, LLC. mail date: Aug. 10, 2010. 8 pages.
PCT Written Opinion for PCT/US2009/044722 filed on May 20, 2009 on behalf of Lawrence Livermore National Security, LLC mail date: Oct. 28, 2010. 6 pages.
PCT International Search Report for PCT/US2009/044722 filed on May 20, 2009 on behalf of Lawrence Livermore National Security, LLC mail date: Oct. 28, 2010. 4 pages.
PCT International Preliminary Report on Patentability for PCT/US2009/044722 filed on May 20, 2009 on behalf of Lawrence Livermore National Security, LLC mail date: Nov. 23, 2010. 7 pages.
International Preliminary Report on Patentability for PCT/US2008/063307 mailed on Nov. 19, 2009 7 pages.
Restriction Requirement issued for U.S. Appl. No. 12/352,548, filed Jan. 12, 2009 in the name of Brett A. Chromy et al.; mail date: Apr. 25, 2011. 6 pages.
Non-Final Office Action issued for U.S. Appl. No. 12/352,548, filed Jan. 12, 2009 in the name of Brett A. Chromy et al.; mail date: Sep. 13, 2011.19 pages.
Non-Final Office Action issued for U.S. Appl. No. 12/118,396, filed May 9, 2008 in the name of Matthew A. Coleman et al.; mail date: Aug. 30, 2011. 15 pages.

Chefson, A. et al."Progess towards the easier use of P450 enzymes", *Mol. bioSyst.*, 2006, 2, 462-469.
Stryer et al., "Oxygen Binds to a Heme Prosthetic Group, Biochemistry" 1995, 4th edition, 148.
Notice of Allowance for U.S. Appl. No. 12/352,548, filed Jan. 12, 2009 in the name of Brett A. Chromy et al., mail date: Mar. 12, 2012. 5 pages.
Gorrod, et al., "Some observations on Type I and Type II microsomal binding spectra", Xenobiotica 1971, 1: 521-522.
Chen, et al., Amino acids in SRS1 and SRS6 are critical for furanocoumarin metabolism by CYP6B1v1, a cytochrome P450 monooxygenase, Insect Mol. Biol. 2002, 11: 175-186.
Das et al., Role of Fe-hydrogenase in biological hydrogen production, Current Science 2006, 90: 1627-1637.
Gilbert, L., Insect Development: morphognesis and metamorphosis, Academic Press, Sep. 18, 2009, pp. 573-574.
Definition of Hydrogenase retrieved from en.wikipedia.org/wiki/Hydrogenase on Nov. 6, 2012, pp. 1-4.
Lodish, H., et al., Section 17.5 Insertion of Membrane Proteins into the ER membrane, Molecular Cell Biology 4th ed. 2000, New York, NY. 9 pages.
White, SH, et al., How Translocons Select Transmembrane Helices, Annu. Rev. Biophys. 2008, 37: 23-42.
Petrakova et al., Noncytopathic replication of Venezuelan equine encephalitis virus and eastern equine encephalitis virus replicons in Mammalian cells. J Virol 79, 7597-608 (2005).
Konishi et al. "Proper maturation of the Japanese encephalitis virus envelope glycoprotein requires co-synthesis with the premembrane protein". J Virol 67, 1672-5 (1993).
Widman et al. Construction and characterization of a second-generation pseudoinfectious West Nile virus vaccine propagated using a new cultivation system. Vaccine 26, 2762-71 (2008).
Fischer, N., et al., "Immobilization of His-Tagged Proteins on Nickel-Chelating Nanolipoprotein Particles". Bioconjugate Chemistry 20, 460-5 (2009).
Lam, K. S., "Application of combinatorial library methods in cancer research and drug discovery" Anticancer Drug Des. (1997) pp. 145-167.
R. A. Sperling, et al. "Surface modification, functionalization and bioconjugation of colloidal inorganic nanoparticles". Phil. Trans. R. Soc. A (2010) vol. 368 No. 1915 pp. 1333-1383.
Yoon et al. "Three-Dimensional Graphene Nano-Networks with High Quality and Mass Production Capability via Precursor-Assisted Chemical Vapor Deposition" Scientific Reports (2013) 3:1788, 1-8.
Whorton M. et al. "A monomeric G protein-coupled receptor isolated in a high-density lipoprotein particle efficiently activates its G protein" Proc Natl Acad Sci US A 104, 7682-7. May 1, 2007.
Dawson P. et al. "Synthesis of Native Proteins by Chemical Ligation" (2000), Ann Rev Biochem 69: pp. 923-960.
Terpe, K., "Overview of tag protein fusions: from molecular and biochemical fundamentals to commercial systems". Appl Microbiol Biotechnol, 60,523-33 (2003).
Kolb, H et al., "The growing impact of click chemistry on drug discovery". Drug Discovery. Today, 8, 1128-37 (2003).
Martin, B.R. and Cravatt, B.F., Large-scale profiling of protein palmitoylation inmammalian cells. Nat. Methods 6, 135-38 (2009).
T. Gardner et al. "Systems for Orthogonal Self-Assembly of Electroactive Monolayers on Au and ITO: An Approach to Molecular Electronics," JACS 1995, 117:6927-6933.
G.H. McGall et al. "The Efficiency of Light-Directed Synthesis of DNA Arrays on Glass Substrates," J. Amer. Che. Soc. 1997, 119:5081-5090.
M. Schena et al. "Quantitative Monitoring of Gene Expression Patterns with a Complementary DNA Microarray," Science, 1995, 270:467-470.
S. Singh-Gasson et al. "Maskless fabrication of light-directed oligonucleotide microarrays using a digital micromirror array," Nature Biotech. 1999, 17:974-978.
Simon, S.R. and Konigsberg, W.H., Chemical modification of hemoglobins: a study of conformation restraint by internal bridging. Proc. N.A.S. USA, 56, 749-56 (1966).
Hein, C.D., Liu, X-M, and Wang, D. 2008. Click Chemistry, A Powerful Tool for Pharmaceutical Sciences. Pharmaceutical Research, vol. 25, No. 10:2216-2230.

(56) References Cited

OTHER PUBLICATIONS

Dalpke et al. 2002. Phosphodiester CpG oligonucleotides as adjuvants: polyguanosine runs enhance cellular uptake and improve immunostimulative activity of phosphodiester CpG oligonucleotides in vitro and in vivo. Immunology 106:102-112.
Weermata, R.D., McCluskie, M.J., Xu, Y., and Davis, H.L. 2000. CpG DNA induces stronger immune responses with less toxicity than other adjuvants. Vaccine 18:1755-62.
Ueda H et al., Induction of tumor necrosis factor-a in solid tumor region by the orally administered synthetic muramyl dipeptide analogue, romurtide (2001) Int'l Immunopharm. 1:97-104.
Osada Y et al., Polymorphonuclear Leukocyte Activation by a Synthetic Muramyl Dipeptide Analog (1982) Inf. Immun. 38:848-854.
Huleatt, et al. 2008. Potent immunogenicity and efficacy of a universal influenza vaccine candidate comprising a recombinant fusion protein linking influenza M2e to the TLR5 ligand flagellin. Vaccine 26:201-214.
Hamdy, S., Haddadi, A., Somayaji, V., Ruan, D. and Samuel, J. 2007. Pharmaceutical analysis of synthetic 77 lipid A-based vaccine adjuvants in poly (d,l-lactic-co-glycolic acid) nanoparticle formulations. Journal of Pharmaceutical and Biomedical Analysis 44:914-923.
Giannin et al. 2006. Enhanced humoral and memory B cellular immunity using HPV16/18 L1 VLP vaccine formulated with the MPL/aluminium salt combination (AS04) compared to aluminium salt only. Vaccine 24:5937-5949.
Fitzgerald, K.A. and Golenbock, D.T. 2007. The Shape of Things to Come. Science 316:1573-1576.
Behrens S., et al., Linking Microbial Phylogeny to Metabolic Activity at the Single-Cell Level by Using Enhanced Element Labeling-Catalyzed Reporter Deposition Fluorescence In Situ Hybridization (EL-FISH) and NanoSIMS, Appl. Environ. Microbiol. 2008, 74: 3143-3150.
Radajewski S., et al., Identification of active methylotroph populations in an acidic forest soil by stable isotope probing, Microbiol. 2002, 148: 2331-2342.
Manefield , M., et al., RNA Stable Isotope Probing, a Novel Means of Linking Microbial Community Function to Phylogeny, Applied and environmental microbiology, 2002, 68: 5367-5373.
Uhlik O., et al., DNA-based stable isotope probing: a link between community structure and function, Science of the Total Environ. 2009, 407: 3611-3619.
Addison SL, et al., Stable isotope probing: Technical considerations when resolving 15N-labeled RNA in gradients, J. Microbiol. Methods 2010, 80: 70-75.
Boschker HTS, et al., The contribution of macrophyte-derived organic matter to microbial biomass in salt-marsh sediments: Stable carbon isotope analysis of microbial biomarkers, Limnol. Oceanogr. 1999, 44: 309-319.
Ouverney C., et al., Combined Microautoradiography-16S rRNA Probe Technique for Determination of Radioisotope Uptake by Specific Microbial Cell Types In Situ, Applied and environmental microbiology 1999, 65: 1746-1752.
Adamcyzk, J., et al., The Isotope Array, a New Tool That Employs Substrate-Mediated Labeling of rRNA for Determination of Microbial Community Structure and Function, Applied and environmental microbiology 2003, 69: 6875-6887.
Brodie EL et al., Application of a High-Density Oligonucleotide Microarray Approach to Study Bacterial Population Dynamics during Uranium Reduction and Reoxidation, Applied and environmental microbiology 2006, 72: 6288-6298.
Cline MS et al., Integration of biological networks and gene expression data using Cytoscape, Nat. Protocols 2007, 2: 2366-2382.
Ludwig W et al., ARB: a software environment for sequence data, Nuc. Acids Res. 2004, 32: 1363-1371.

Bijsterbosch MK et al., Specific targeting of a lipophilic prodrug of iododeoxyuridine to parenchymal liver cells using lactosylated reconstituted high density lipoprotein particles, Biochem. Pharma 1996, 52: 113-121.
Jasanada F et al., Indium-111 labeling of low density lipoproteins with the DTPA—Bis(stearylamide): Evaluation as a Potential Radiopharmaceutical for Tumor Localization, Biocon. Chem. 1996, 7: 72-81.
Masquelier M et al., Low-density lipoprotein as a carrier of antitumoral drugs: in vivo fate of drug-human low-density lipoportien complexes in mice, Cancer Res. 1986, 46: 3842-3847.
Brodie E et al., Profiling microbial identity and activity: Novel applications of NanoSIMS and High Density Microarrays, Systems Biology Research Strategy & Technology Development, Genomics: GTL Awardee Workshop VI, Dept. of Energy 2008, 93-94.
Rusinol AE et al., In Vitro Reconstitution of Assembly of Apolipoprotein B48-containing Lipoproteins, J. Biol. Chem. 1997, 272: 8019-8025.
Walter P et al., Preparation of Microsomal Membranes for Cotranslational Protein Translocation, Methods in Enzymology 1983, 96: 84-93.
Ntc of Allowance mailed on Apr. 25, 2014 for U.S. Appl. No. 12/352,548, filed Jan. 12, 2009 in the name of Brett A. Chromy et al. 9 pages.
Ntc of Allowance mailed on Aug. 5, 2014 for U.S. Appl. No. 12/352,548, filed Jan. 12, 2009 in the name of Brett A. Chromy et al. 8 pages.
Final Office Action mailed on Oct. 24, 2011 for U.S. Appl. No. 12/469,533, filed May 20, 2009 in the name of Paul D. Hoeprich et al. 11 pages.
Patel J et al., Preparation and Characterization of Nickel Nanoparticles for Binding to His-tag Proteins and Antigens, Pharma. Res. 2007, 24: 343-352.
Ruger R et al., In vitro characterization of binding and stability of single-chain Fv Ni-NTA-liposomes, J. Drug Targeting 2006, 14: 576-582.
Schnell DJ et al., Protein Translocons: Multifunctional Review Mediators of Protein Translocation across Membranes, Cell 2003, 112: 491-505.
Baas, B. J., Denisov, I. G., and Sligar, S. G. (2004) "Homotropic cooperativity of monomeric cytochrome P450 3A4 in a nanoscale native bilayer environment", Arch Biochem Biophys 430, 218-228.
Baker et al., "Hydrogen Production by a Hyperthermophilic Membrane-Bound Hydrogenase in Water Soluble Nanolipoprotein Particles" (2009), J. Amer. Chem. Soc., 131 (2):7508-7509. (15 pages).
Bayburt, T. H., and Sligar, S. G. (2002) "Single-molecule height measurements on microsomal cytochrome P450 in nanometer-scale phospholipid bilayer disks", Proc Natl Acad Sci U S A, 99, 6725-6730.
Bayburt, T. H., Leitz, A. J., Xie, G., Oprian, D. D., and Sligar, S. G. (2007) "Transducin activation by nanoscale lipid bilayers containing one and two rhodopsins", J Biol Chem, 282 (20), 14875-14881.
Boschker et al., "Direct linking of microbial populations to specific biogeochemical processes by 13C-labelling of biomarkers", Nature, 392, 801-805 (1998).
Brodie et al., "Urban aerosols harbor diverse and dynamic bacterial populations". Proceedings of the National Academy of Sciences 104 (1), 299-304 (Jan. 2, 2007).
Cappucchio J. et al., "Cell-free Co-expression of Functional Membrane Proteins and Apolipoprotein, Forming Soluble Nanolipoprotein Particles", Molecular and Cellular Proteomics 7.11 (2008) pp. 2246-2253.
Casey P.J.; M. C. Seabra, (1996). "Protein Prenyltransferases". Journal of Biological Chemistry 271 (10): 5289-5292.
Gronover et al. (2011). "Natural Rubber Biosynthesis and Physic-Chemical Studies on Plant Derived Latex" in Biotechnology of Biopolymers, Magdy Elnashar (Ed.), ISBN: 978-953-307-179-4. pp. 75-88.
Radajewski et al., Stable-isotope probing as a tool in microbial ecology. Nature 403, 646-649 (2000).
Jones, M. et al. "Computer programs to identify and classify amphipathic helical domains" Journal of Lipid Research, vol. 33, pp. 287-296, 1992.

(56) References Cited

OTHER PUBLICATIONS

Fischer, N. et al. "Evaluation of Nanolipoprotein Particles (NLPs) as an In Vivo Delivery Platform" PLoS ONE 9(3): e93342, Mar. 1-17, 2014.
Klammt, C. et al. "Cell-free production of G protein-coupled receptors for functional and structural studies". J. Struct. Biol. 158, 482-493, Jul. 2007.
Restriction Requirement mailed on Dec. 8, 2014 for U.S. Appl. No. 14/199,973, filed Mar. 6, 2014 in the name of Paul D. Hoeprich. 7 pages.
Non-Final Office Action mailed on May 6, 2015 for U.S. Appl. No. 14/199,973, filed Mar. 6, 2014 in the name of Paul D. Hoeprich. 34 pages.
Advisory Action mailed on Jul. 23, 2015 for U.S. Appl. No. 12/118,530, filed May 9, 2008 in the name of Matthew A. Coleman. 13 pages.
Cornish et al., "Rubber Biosynthesis in Plants", American Oil Chemist Society, The Lipid Library, Nov. 2, 2011. 1-10.
Cornish, K. et al., "Natural Rubber Biosynthesis in Plants: Rubber Transferase" Methods in Enzymology, (2012) vol. 515, pp. 63-82.
Cruz, F. et al. (2007) "Kinetic properties of recombinant MAO-A on incorporation into phospholipid nanodisks", *J Neural Transm*, 114, 699-702.
Desantis et al., "Greengenes, a Chimera-Checked 16S rRNA Gene Database and Workbench Compatible with ARB", *Appl. Environ. Microbiol.* 72 (7), 5069-5072 (2006).
Desantis et al., "High-Density Universal 16S rRNA Microarray Analysis Reveals Broader Diversity than Typical Clone Library When Sampling the Environment", *Microbial Ecology* 53, 371-383 (2007).
Donniger et al., "An Improved Synthesis of Isopentenyl Pyrophosphate", (1967) Biochem. J. 105:545-547.
Frydman et al. (1996) "Principles of chaperone-assisted protein folding: differences between in vitro and in vivo mechanisms", *Science* 272, 1497-1502.
Greve, "Ullman's Encyclopedia of Industrial Chemistry, Rubber, 2. Natural", 2012, Wiley-VCH Verlag GmbH & Co., KGaA, Weinheim, DOI: 10.1002/14356007.a23_225, pp. 583-596.
Hiraishi, et al. "Enzyme-catalyzed Synthesis and Degradation of Biopolymers", Mini-Reviews in Organic Chemistry, vol. 6, No. 1, Feb. 2009, pp. 44-54(11) Bentham Science Publishers.
Ishihara, G. et al.. (2005) "Expression of G protein coupled receptors in a cell-free translational system using detergents and thioredoxin-fusion vectors", *Protein Expr Purif* 41, 27-37.
Jonas et al. (1989) "Defined apolipoprotein A-I conformations in reconstituted high density lipoprotein discs", *J Biol Chem* 264, 4818-4824.
Katzen et al. "Insertion of Membrane Proteins into Discoidal Membranes using a Cell-free Protein Expression Approach" (2008) J. Proteome Res., vol. 7, No. 8, 3535-3542; ASAP Article; DOI: 10.1021/pr800265f.
Lechene et al., "High-resolution quantitative imaging of mammalian and bacteria cells using stable isotope mass spectrometry" *Journal of Biology* (2006) 5:20, published on line at the pagejbiol.com/content/5/6/20. 30 pages.
Ohya et al., (2001). "Biosynthesis of Natural Rubber and Other Natural Polyisoprenoids". Biopolymers Polyisoprenoids. 2, 73-81.
Paterson-Jones, , "The Biosynthesis of Natural Rubber", Journal of Plant Physiology, vol. 136, Issue 3, Jun. 1990, pp. 257-263.
Peters-Libeu, C. A., et al. (2006) "Model of biologically active apolipoprotein E bound to dipalmitoylphosphatidylcholine", *J Biol Chem* 281 (2), 1073-1079.
Cornish et al. "Characterization of *cis*-prenyl transferase activity localized in a buoyant fraction of rubber particles from *Ficus elastica* latex", Plant Physiol. Biochem. 1996; 34 (3): 377-384.
Ponciano et al. "Transcriptome and gene expression analysis in cold-acclimated guayule (*Parthenium argentum*) rubber-producing tissue", (2012) Phytochemistry 79:57-66.
Rensen P.C.N. et al., "Recombinant Lipoproteins: Lipoprotein-Like Lipid Particles for Drug Targeting" (2001) Adv. Drug Delivery Reviews. Elsevier, 47:251-276.
Sawasaki et al. (2002) "A bilayer cell-free protein synthesis system for high-throughput screening of gene products", *FEBS Lett* 514, 102-105.
Schmidt et al. "Characterization of rubber particles and rubber chain elongation in *Taraxacum koksaghyz*", (2010) BMC Biochemistry 11:1-11.
Shaw et al. (2004) "Phospholipid phase transitions in homogeneous nanometer scale bilayer discs", *FEBS Lett* 556, 260-264.
Siler et al. "Composition of rubber particles of *Hevea brasiliensis, Parthenium argentatum, Ficus elastics* and *Euphorbia lactiflua* indicates unconventional surface structure" (1997) Plant Physiol. Biochem. 35 (11):881-889.
Singh et al, "The micromorphology and protein characterization of rubber particles in *Ficus carica, Ficus benghalensis* and *Hevea brasiliensis*" in Journal of Experimental Botany vol. 54, No. 384, pp. 985-992, Mar. 2003.
Stadermann, et al., "Nanosims: The Next Generation Ion Probe for Microanalysis of Extraterrestraisl Material", *Meteoritics & Planetary Science* 34 (4), A111-112 (1999).
Vuorilehto et al., "Indirect electrochemical reduction of nicotinamide coenzymes", Bioelectrochemistry 65 (2004) 1-7.
Wallin et al. (1998) "Genome-wide analysis of integral membrane proteins from eubacterial, archaean, and eukaryotic organisms", *Protein Sci* 7, 1029-1038.
Whalen et al, "Chapter 23: Development of Crops to Produce Industrially Useful Natural Rubber" of T.J. Bach and M. Rohmer (eds.), Isoprenoid Synthesis in Plants and Microorganisms: New Concepts and Experimental Approaches, Springer Science+Business Media New York, 2013. 329-345.
Xie, et al. "Initiation of rubber synthesis: In vitro comparisons of benzophenone modified diphosphate analogues in three rubber producing species", Phytochemistry, 69 (2008) 2539-2545.
Cornish et al., "The Major Protein of Guayule Rubber Particles Is a Cytochrome P450", The Journal of Biological Chemistry, vol. 270, No. 15, Apr. 14, 1995, pp. 8487-8494.
Final Office Action issued for U.S. Appl. No. 12/118,530, filed May 9, 2008 in the name of Matthew A. Coleman. Mail date: Mar. 6, 2015. 52 pages.
Final Office Action issued for U.S. Appl. No. 12/118,396, filed May 9, 2008 in the name of Matthew A. Coleman. Mail date: Feb. 4, 2015. 29 pages.
Non-Final Office Action issued for U.S. Appl. No. 12/469,533, filed May 20, 2009 in the name of Paul D. Hoeprich. Mail date: May 23, 2012. 15 pages.
Restriction Requirement issued for U.S. Appl. No. 12/604,362, filed Oct. 22, 2009 in the name of Paul D. Hoeprich. Mail date: Jan. 11, 2012. 8 pagse.
Non-Final Office Action issued for U.S. Appl. No. 12/604,362, filed Oct. 22, 2009 in the name of Paul D. Hoeprich. Mail date: May 7, 2012. 12 pages.
Final Office Action issued for U.S. Appl. No. 12/604,362, filed Oct. 22, 2009 in the name of Paul D. Hoeprich. Mail date: Dec. 4, 2012. 8 pages.
Notice of Allowance issued for U.S. Appl. No. 12/604,362, filed Oct. 22, 2009 in the name of Paul D. Hoeprich. Mail date: Jul. 30, 2014. 13 pages.
Restriction Requirement issued for U.S. Appl. No. 13/023,468, filed Feb. 8, 2011 in the name of Jennifer Pett-Ridge. Mail date: Aug. 31, 2012. 5 pages.
Non-Final Office Action issued for U.S. Appl. No. 13/023,468, filed Feb. 8, 2011 in the name of Jennifer Pett-Ridge. Mail date: Oct. 26, 2012. 36 pages.
Kim et al., "Gold Nanoparticle-Enhanced Secondary Ion Mass Spectrometry Imaging of Peptides on Self-Assembled Monolayers", Anal. Chem., 78 (6), (2006), p. 1913-1920.
Restriction Requirement issued for U.S. Appl. No. 14/199,973, filed Mar. 6, 2014 in the name of Paul D. Hoeprich. Mail date: Dec. 8, 2014. 7 pages.

(56) References Cited

OTHER PUBLICATIONS

Non-Final Office Action issued for U.S. Appl. No. 14/199,973, filed Mar. 6, 2014 in the name of Paul D. Hoeprich. Mail date: May 6, 2015. 34 pages.
Unger et al., "The Genetic Algorithm Approach to Protein Structure Prediction", Structure and Bonding (2004) 110: 153-175.
Guo et al., "Protein tolerance to random amino acid change", 2004, Proc. Natl. Acad. Sci. USA 101 (25): 9205-9210.
Lazar et al., "Transforming Growth Factor α: Mutation of Aspartic Acid 47 and Leucine 48 Results in Different Biological Activities", 1988, Mol. Cell. Bioi. 8 (3):1247-1252.
Hill et al., "Functional Analysis of conserved Histidines in ADP-Glucose Pyrophosphorylase from *Escherichia coli*", 1998, Biochem. Biophys. Res. Comm. 244:573-577.
Wacey et al., "Disentangling the perturbational effects of amino acid substitutions in the DNA-binding domain of p53", Hum Genet, 1999, vol. 104, pp. 15-22.
Berthelot et al., "Rubber Elongation Factor (REF), a Major Allergen Component in *Hevea brasiliensis* Latex Has Amyloid Properties", PLoS One (Epub Oct. 25, 2012), vol. 7 (10), pp. 1-12.
Cornish, "Biochemistry of natural rubber, a vital raw material, emphasizing biosynthetic rate, molecular weight and compartmentalization, in evolutionarily divergent plant species", Nat. Prod. Rep., (2001), vol. 18, pp. 182-189.
Branden et al. "Introduction to Protein Structure" (1999), 2nd edition, Garland Science Publisher, pp. 3-12.
Lluis et al., "Protein Engineering Methods Applied to Membrane Protein Targets" (2013) 26 (2): 91-100.
Boldog et al., "Using Nanodiscs to Create Water-Soluble Transmembrane Chemoreceptors Inserted in Lipid Bilayers", Methods in Enzymology, vol. 423, 317-335 (2007).
Burgdorf et al., "The Soluble NAD+-Reducing [NiFe]-Hydrogenase from *Ralstonia eutropha* H16 Consists of Six Subunits and Can Be Specifically Activated by NADPH", Journal of Bacteriology, 187 (9), 3122-3132 (2005).
Das et al., "Hydrogen production by biological processes: a survey of literature", International Journal of Hydrogen Energy, 26 (2001), 13-28.
Duan et al., "Co-incorporation of heterologously expressed *Arabidopsis* cytochrome P450 and P450 reductase into soluble nanoscale lipid bilayers", Archives of Biochemistry and Biophysics, 424 (2004) 141-153.
Dubey et al., "Microencapsulation Technology and Applications", Defence Science Journal, 59 (1), 82-95 (2009).
Gan et al., "Role of NADPH-Cytochrome P450 Reductase and Cytochrome-$b_5$/NADH-$b_5$ Reductase in Variability of CYP3A Activity in Human Liver Microsomes", Drug Metabolism and Disposition, 37 (1), 90-96 (2009).
Hallenbeck et al., "Biological hydrogen production: fundamentals and limiting processes", International Journal of Hydrogen Energy, 27 (11-12), 1185-1193 (2002).
Hasemann et al., "Structure and function of cytochromes P450: a comparative analysis of three crystal structures", Structures, 3 (1), 41-62 (1995).
Kapdan et al., "Bio-hydrogen production from waste materials", Enzyme and Microbial Technology, 38 (2006) 569-582.
Kurkin et al., "The membrane-bound [NiFe]-hydrogenase (Ech) from *Methanosarcina barkeri*; unusual properties of the iron-sulphur clusters", Eur. J. Biochem., 269, 6101-6111 (2002).
Long et al., "Characterization of a HoxEFUYH type of [NiFe] hydrogenase from *Allochromatium vinosum* and some EPR and IR properties of the hydrogenase module", J. Biol. Inorg. Chem., 12, 62-78 (2007).
McIntosh et al., "The [NiFe]-Hydrogenase of the Cyanobacterium *Synechocystis* sp. PCC 6803 Works Bidirectionally with a Bias to $H_2$ Production", Journal of the American Chemical Society, 133, 11308-11319 (2011).
McTernan et al., "Intact Functional Fourteen-subunit Respiratory Membrane-bound [NiFe]-Hydrogenase Complex of the Hyperthermophilic Archaeon *Pyrococcus furiosus*", The Journal of Biological Chemistry, 289 (28) 19364-19372 (2014).
McTernan et al., "Intact Functional Fourteen-subunit Respiratory Membrane-bound [NiFe]-Hydrogenase Complex of the Hyperthermophilic Archaeon *Pyrococcus furiosus*", The Journal of Biological Chemistry, 289 (28) 19364-19372 (2014). *Supplemental material*.
Meuer et al., "Purification and catalytic properties of Ech hydrogenase from *Methanosarcina barkeri*", Eur. J. Biochem., 265, 325-335 (1999).
Rakhely et al., "Cyanobacterial-Type, Heteropentameric, NAD+-Reducing NiFe Hydrogenase in the Purple Sulfur Photosynthetic Bacterium *Thiocapsa roseopersicina*", Applied and Environmental Microbiology, 70 (2), 722-728 (2004).
Schmitz et al., "HoxE-a subunit specific for the pentameric bidirectional hydrogenase complex (HoxEFUYH) of cyanobacteria", Biochimica et Biophysica Acta, 1554, 66-74 (2002).
Soboh et al., "Purification and catalytic properties of a CO-oxidizing: H2-evolving enzyme complex from *Carboxydothermus hydrogenoformans*" Eur. J. Biochem., 269, 5712-5721 (2002).
Soboh et al., "A multisubunit membrane-bound [NiFe] hydrogenase and an NADH-dependent Fe-only hydrogenase in the fermenting bacterium *Thermoanaerobacter tengcongenis*", Microbiology, 150, 2451-2463 (2004).
Wikipedia—Bacteriorhodopsin (Downloaded from the internet on Jun. 22, 2015). 2 pages total.
Zhanhua et al., "Protein subunit interfaces: heterodimers versus homodimers", Bioinformation, 1 (2); 28-39 (2005).
Barros, F., et al., Modulation of human erg K+ channel gating by activation of a G protein-coupled receptor and protein kinase C, J. Physiology 1998, 511: 333-346.
Dong, F., et al., Endothelin-1 enhances oxidative stress, cell proliferation and reduces apoptosis in human umbilical vein endothelial cells: role of ETB receptor, NADPH oxidase and caveolin-1 British J. of Pharmacology 2005, 145: 323-333.
Dumartin, B., et al., Dopamine tone regulates D1 receptor trafficking and delivery in striatal neurons in dopamine transporter-deficient mice, PNAS 2000, 97: 1879-1884.
Gantz, I., et al.,Molecular cloning of a gene encoding the histamine H2 receptor, PNAS 1991, 88: 429-433.
Hauger, R., et al., Corticotropin Releasing Factor (CRF) Receptor Signaling in the Central Nervous System: New Molecular Targets, CNS Neurol. Discord. Drug Target 2006, 5: 453-479.
Hong, Y. et al., G-Protein-Coupled Receptor Microarrays for Multiplexed Compound ScreeningJ. Biomol. Screening 2006, 11: 435-438.
Metz, J., et al ACTH, a-MSH, and control of cortisol release: cloning, sequencing, and functional expression of the melanocortin-2 and melanocortin-5 receptor in *Cyprinus carpio*Am. J. Physiol. Regul. Integr. Comp. Physiol. 2005, 289: R814-R826.
Pettibone, D., et al., The Effects of Deleting the Mouse Neurotensin Receptor NTR1 on Central and Peripheral Responses to NeurotensinJ. Pharma. & Exp. Therapeutics 2002, 300: 305-313.
Ren, X., et al., Different G protein-coupled receptor kinases govern G protein and b-arrestin-mediated signaling of V2 vasopressin receptor, PNAS 2005, 102: 1448-1453.
Adrenergic Receptor, Wikipedia 2006, ://web.archive.org/web/20061230132111 //en.wikipedia.org/wiki/Adrenergic_Receptor , 4 pages.
5-HT Receptor, Wikipedia 2007, //web.archive.org/web/20071109235348//en.wikipedia.org/wiki/5-HT_receptor 7 pages.
Muscarinic Acetylcholine Receptor, Wikipedia 2007, //web.archive.org/web/20071020193657/:///en.wikipedia.org/wiki/Muscarinic_acetylcholine_receptor 6 pages.
G Protein-coupled Receptor, Wikipedia 2008, ://web.archive.org/web/20080224232212/:///en.wikipedia.org/wiki/G_protein-coupled_receptor 7 pages.
Oded Béjà, et al. Bacterial Rhodopsin: Evidence for a New Type of Phototrophy in the Sea. Science. 2000, 2895.5486: 1902-1906.
Shih, et al. Molecular Dynamics Simulations of Discoidal Bilayers Assembled from Truncated Human Lipoproteins. Biophysical J. 2006, 88: 548-556.

(56) References Cited

OTHER PUBLICATIONS

"Co-Translation of integral membrane proteins (MP) with membrane scaffold proteins (MSP), also known as nanodiscs" //technology.sbkb.org/portal/page/329/ retrieved on Jul. 1, 2015, pp. 1-3.
"Nanodisc Assembly Kit MSP1E3D1_POPC" Cube Biotech, Dec. 2014, pp. 1-3.
"Nanodisc" Kobo eBook Library, http://www.kobolibrary.com/articles/Nanodisc, retrieved on Aug. 4, 2015, pp. 1-4.
"Nanodisc" Trademark #78166119, Owner: Sligar, Stephen G., ://inventively.com/search/trademarks/78166119; retrieved on Aug. 4, 2015. 2 pags.
"Nanodisc Formation" LIAO Lab, Department of Cellbiology, Harvard Medical School, //liao.hms.harvard.edu/node/34; retrieved on Aug. 3, 2015. 2 pages.
"Protocols for Preparation of Nanodiscs" Mar. 4, 2008, pp. 1-7.
Crankshaw, C. "Nanodisc Technology: A Revolutionary System for Study of Membrane Proteins" Biofiles, vol. 8, No. 20, ://www.sigmaaldrich.com/technical-documents/articles/biofiles/nanodisc-technology.html; pp. 1-3 Retrieved on Aug. 4, 2015.
"Assembly of nanodiscs for use in cell-free expression using MSP1D1 protein and POPC phospholipids." Cube Biotech. 3 pgs. 2014.
Lasic et al. "Novel Applications of Liposomes" *Trends Biotechnol.* 1998, 16, 307-321.
Boroske et al. "Osmotic Shrinkage of Giant Egg-Lecithin Vesicles" *Biophys. J.* 1981, 34, 95-109.
Disalvo et al. "Surface changes induced by osmotic shrinkage on large unilamellar vesicles" *Chem. Phys. Lipids* 1996, 84, 35-45.
Choquet et al. "Stability of pressure-extruded liposomes made from archaeobacterial ether lipids" *Appl. Microbiol. Biotechnol.* 1994, 42, 375-384.
Liang et al. "Mechanical properties and stability measurement of cholesterol-containing liposome on mica by atomic force microscopy" *J. Colloid Interface Sci.* 2004, 278, 53-62.
Hernández-Caselles et al. "Influence of liposome charge and composition on their interaction with human blood serum proteins" *Mol. Cell. Biochem.* 1993, 120, 119-126.
Stryer "Lipid Vesicles (Liposomes) and Planar Membranes Are Valuable Model Systems" *Biochemistry, 4th Ed.* W.H. Freeman and Company, New York: 1995, p. 271.
Kostarelos et al. "Steric stabilization of phospholipid vesicles by block copolymers: Vesicle Flocculation and osmotic swelling caused by monovalent and divalent cations" *J. Chem. Soc., Faraday Trans.*, 1998, 94, 2159-2168.

Author Unknown, Special Report, Dengue fever climbs the social ladder, Nature 2007, 448: 734-735.
Gupta, R., et al., Adjuvants for human vaccines—current status, problems and future prospects, Vaccine 1995, 13: 1263-1276.
Okemoto, K., et al., A Potent Adjuvant Monophosphoryl Lipid A Triggers Various Immune Responses, but Not Secretion of IL-1β or Activation of Caspase-1, The Journal of Immunology 2006, 176: 1203-1208.
Mata-Haro, V., et al., The vaccine adjuvant monophosphoryl lipid A as a TRIF-biased agonist of TLR4, Science 2007, 316: 1628-1632.
Persing, D. et al., Taking toll: lipid A mimetics as adjuvants and immunomodulators, Trends in Microbiology 2002, 10: S32-S37.
Zimmermann, et al., Immunostimulatory DNA as adjuvant: efficacy of phosphodiester CpG oligonucleotides is enhanced by 3' sequence modifications (2003) Vaccine 21:990-995.
Chaung, et al., CpG oligodeoxynucleotides as DNA adjuvants in vertebrates and their applications in immunotherapy (2006) Int'l Immunopharm. 6:1586-1596.
Ruger, et al., Generation of immunoliposomes using recombinant single-chain Fv fragments bound to Ni-NTA-liposomes (2005) J. Drug Targeting 13:399-406.
Chikh, et al., Attaching histidine-tagged peptides & proteins to lipid-based carriers through use of metal-ion-chelating lipids (2002) BBA 1567:204-212.
Ulmer, et al., Vaccine manufacturing: challenges and solutions (2006) Nature Biotech. 24:1377-1383.
Blanchette, C.D., et al., Characterization and Purification of Polydisperse Reconstituted Lipoproteins and Nanolipoprotein Particles. International Journal of Molecular Sciences 2009, 10:2958-2971.
Fischer, N.O., et al., Conjugation to Nickel-Chelating Nanolipoprotein Particles Increases the Potency and Efficacy of Subunit Vaccines to Prevent West Nile Encephalitis, Bioconjugate Chem., 2010, vol. 21, pp. 1018-1022.
Ratanabanangkoon, P. et al., Two-Dimensional Streptavidin Crystals on Giant Lipid Bilayer Vesicles, Langmuir 2002, vol. 18, pp. 4270-4276.
Bischler, N. et al, Specific Interaction and Two-Dimensional Crystallization of Histidine Tagged Yeast RNA Polymerase I on Nickel-Chelating Lipids, Biophysical Journal, Mar. 1998, vol. 74, pp. 1522-1532.
Kubalek, E.W. et al., Two-Dimensional Crystallization of Histidine-Tagged, HIV-1 Reverse Transcriptase Promoted by a Novel Nickel-Chelating Lipid, Journal of Structural Biology, 1994, vol. 113, pp. 117-123.

Cell membrane proteins

+ Detergent, Lipid

Apolipoprotein

Membrane protein Nanolipoprotein particles (MP-NLPs)

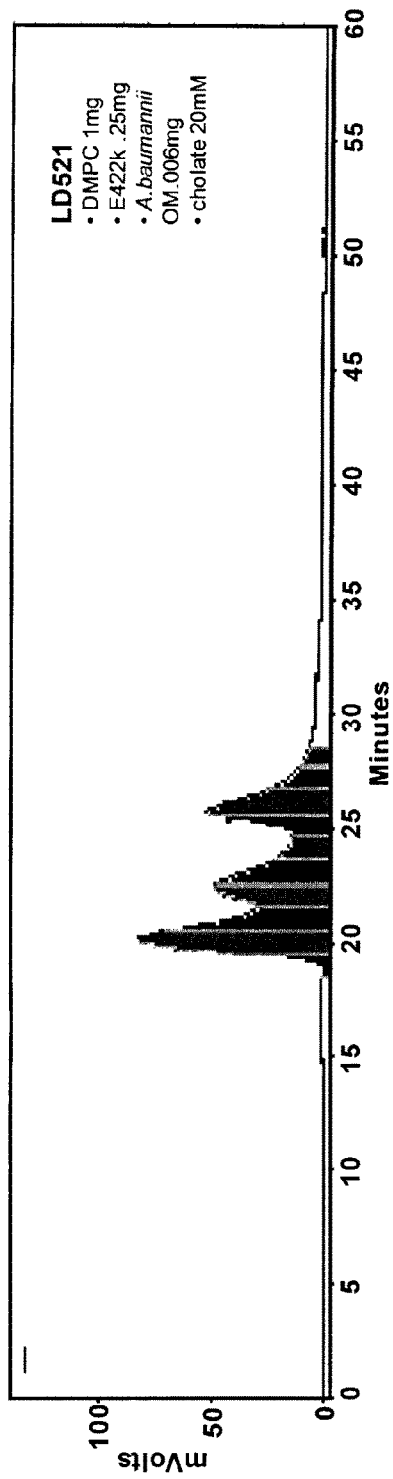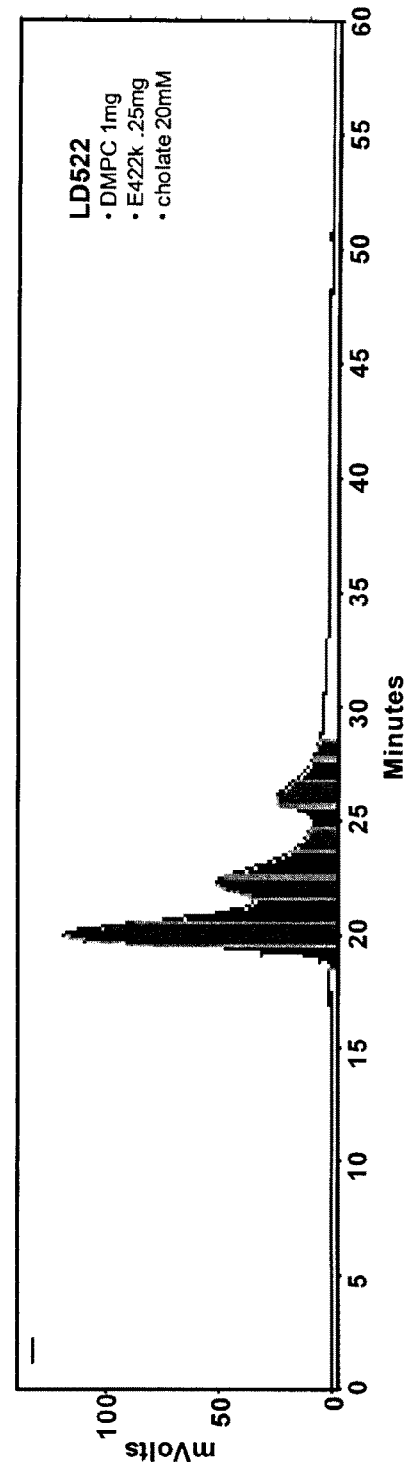

SEC shows successful H-NLPs, smaller than liposomes, larger than empty NLPs

H-NLPs are larger than empty NLPs

| Sample | Mol Wt. | Stokes D |
|---|---|---|
| Empty | 710 kDa | 15.9 |
| 25 ug | 1465 kDa | 21.1 |
| 25 ug | 1500 kDa | 21.3 |
| 10ug | 820 kDa | 16.8 |
| 10ug | 785 kDa | 16.5 |
| No E con | 2240 kDa | 24.9 |

FIG. 18

NANOLIPOPROTEIN PARTICLES AND RELATED METHODS AND SYSTEMS FOR PROTEIN CAPTURE, SOLUBILIZATION, AND/OR PURIFICATION

CROSS REFERENCE TO RELATED APPLICATIONS

This application is a U.S. Continuation Application of U.S. patent application Ser. No. 12/352,548 entitled "Nanolipoprotein Particles And Related Methods And Systems For Protein Capture, Solubilization, And/Or Purification" filed on Jan. 12, 2009, which, in turn, claims priority to U.S. Provisional application entitled "Functional membrane protein capture, solubilization, and purification from native cell membrane fractions using nanolipoprotein particles formed in situ" Ser. No. 61/020,638, filed on Jan. 11, 2008 and to U.S. Provisional application entitled "Hydrogen Production by Membrane Associated Hydrogenases in Soluble Nanolipoprotein Particles" Ser. No. 61/115,446, filed on Nov. 17, 2008, the disclosure of each of which is incorporated herein by reference in its entirety. This application may also be related to U.S. application entitled "Methods and Systems for Monitoring Production of a Target Protein in a Nanolipoprotein Particle" Ser. No. 12/118,530, filed on May 9, 2008, to U.S. application entitled "Methods and Systems for Producing Nanolipoprotein Particle" Ser. No. 12/118,396, filed on May 9, 2008, and to U.S. application entitled "Nanolipoprotein Particles comprising Functional Membrane Associated Biocatalysts and related Assemblies, Methods and Systems", filed on Jan. 12, 2009, the disclosure of each of which is incorporated herein by reference in its entirety.

STATEMENT OF GOVERNMENT GRANT

The United States Government has rights in this invention pursuant to Contract No. DE-AC52-07NA27344 between the U.S. Department of Energy and Lawrence Livermore National Security, LLC.

FIELD

The present disclosure relates to nanolipoprotein particles (NLPs) and in particular to NLPs and related methods and systems for capturing, solubilizing and/or purifying a target protein, and in particular a membrane associated protein.

BACKGROUND

Membrane-associated proteins and protein complexes account for—30% or more of the cellular proteins. Membrane proteins are held within a bilayer structure. The basic membrane bilayer construct consists of two opposing layers of amphiphilic molecules know as phospholipids; each molecule has a hydrophilic moiety, i.e., a polar phosphate group/derivative, and a hydrophobic moiety, i.e., a long hydrocarbon chain. These molecules self-assemble in a biological (largely aqueous) environment according to thermodynamics associated with water exclusion or hydrophobic association.

In order to facilitate the myriad functions of biological membranes including the passage of nutrients, signaling molecules and other molecules into and out of the cell, membrane proteins are arrayed in the bilayer structure. In particular, some proteins span the bilayer, others are anchored within the bilayer, and still others organize "peripheral" proteins into complexes. Many membrane bound protein complexes mediate essential cellular processes e.g. signal transduction, transport, recognition, and cell-cell communication.

In general, this class of proteins is challenging to study because of their insolubility and tendency to aggregate when removed from their protein lipid bilayer environment. Generally, although membrane proteins are optimally folded and functional when in a lipid bilayer, certain standard protein purification methods often remove lipids, invariably altering protein conformation and function.

Additionally, certain organisms, such as gram negative bacteria or plants, have membranes (e.g. outer membrane of gram negative bacteria), that are structurally different than the typical bilayer. Furthermore in gram negative bacteria, some membrane associated proteins span the inner membrane and outer membrane of the bacteria. Purification of membrane associated proteins from those organisms can be particularly challenging and many of those proteins often do not maintain their function following extraction.

The above challenges often make derivation and study of membrane proteins and membrane proteomes particularly difficult due to the complex structure and solubility of all the membrane proteins in a particular membrane fraction.

SUMMARY

Provided herein, are methods, which, in several embodiments, allow assembling, solubilizing and/or purifying in a NLP, membrane associated proteins of any size, number and/or type in their functional form to the extent of allowing comprehensive proteomic analysis of several kinds of membranes, including outer membrane of gram negative bacteria and membranes of plant cells.

According to a first aspect, a method for assembling a membrane associated protein with a scaffold protein, and a membrane forming lipid into a nanolipoprotein particle, is described. The membrane forming lipid has a membrane forming lipid gel-crystalline transition temperature, and the method comprises: contacting the membrane associated protein with the scaffold protein and the membrane forming lipid to provide an admixture. The method further comprises subjecting the admixture to a temperature transition cycle in presence of a detergent, for a time and under condition to allow assembly of the nanolipoprotein particle. In the method, the temperature transition cycle comprises: a temperature increase step and a temperature decrease step. In the temperature increase step the admixture is brought to a temperature above the membrane forming lipid gel crystalline transition temperature. In the temperature decrease step the admixture is brought to a temperature below the membrane forming lipid gel crystalline transition temperature.

According to a second aspect, a method for solubilizing a membrane associated protein comprised in a cell membrane is described. The method comprises: contacting the cell membrane with a scaffold protein and a membrane forming lipid to provide an admixture. The method further comprises subjecting the admixture to a temperature transition cycle in presence of a detergent, for a time and under condition to allow assembly of a nanolipoprotein particle comprising a solubilized membrane associated protein. In the method, the membrane forming lipid has a membrane forming lipid gel-crystalline transition temperature; and the temperature transition cycle comprises: a temperature increase step wherein the admixture is brought to a temperature above said membrane forming lipid gel crystalline transition temperature and a temperature decrease step wherein the admixture is brought to a temperature below said membrane forming lipid gel crystalline transition temperature.

According to a third aspect, a method for purifying a membrane associated protein from a cell membrane into a nanolipoprotein particle is disclosed, the method comprises: contacting the cell membrane with a scaffold protein and a membrane forming lipid to provide an admixture, and subjecting the admixture to a temperature transition cycle in presence of a detergent, for a time and under condition to allow assembly of a nanolipoprotein particle comprising the target protein. The method can further comprise isolating the target protein from the nanolipoprotein particle. In the method, the membrane forming lipid has a membrane forming lipid gel-crystalline transition temperature and the temperature transition cycle comprises: a temperature increase step wherein the admixture is brought to a temperature above said membrane forming lipid gel crystalline transition temperature and a temperature decrease step wherein the admixture is brought to a temperature below said membrane forming lipid gel crystalline transition temperature.

The methods herein described can be used, in several embodiments, to assemble, solubilize and/or purify in the NLPs any kind of membrane protein of interest, including integral membrane proteins and other proteins difficult to manipulate with current methods.

The methods herein described can also be used, in several embodiments, to assemble, solubilize and/or purify in the NLPs of any size including complex membrane proteins formed by several subunits.

The methods herein described can further be used, in several embodiments, to assemble, solubilize and/or purify in the NLPs a controlled number of membrane associated proteins to the extent of allowing a proteomic analysis of a membrane or membrane fraction that is more comprehensive and/or performed with a more simplified procedure, if compared to several current methods.

The methods herein described can also be used, in several embodiments, to assemble, solubilize and/or purify in the NLPs, membrane associated proteins from a wide variety of membrane fractions, including crude membrane preparations of inner and outer membranes of gram-negative bacteria, single bilayer membranes of gram-positive bacteria, and plasma membranes of eukaryotic cells, including yeasts cells and plant cells.

The methods herein described can further be used, in several embodiments, to assemble, solubilize and/or purify in the NLPs, membrane associated proteins in their functional form, thus allowing, harvest, reproduction and/or further analysis of the proteins' structure and activity, as well as the interaction with other proteins.

The methods herein described allow, in several embodiments isolation and harvest of non-recombinantly derived membrane proteins from a variety of cell types, including their native membrane environment.

The methods and systems herein described can be also used in connection with protein purification, membrane protein structure/function, countermeasure discovery, therapeutic discovery, vaccine development, detection of agents that are detrimental to normal cellular function.

In particular, methods and systems herein disclosed can be used, in several embodiments, for performing the purification of membrane proteins simply and easily. Protein purification, membrane protein structure/function, proteomic analysis, countermeasure discovery, therapeutic discovery, vaccine development, and detection of pathogens or poisons can all be enhanced using the methods described herein.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description and the examples, serve to explain the principles and implementations of the disclosure.

FIG. 3A shows an NLP assembly that gives rise to a single SEC peak that corresponds to a homogeneous preparation of NLPs for the purpose of incorporating a large membrane protein or a significant number of membrane proteins. FIG. 3B shows an NLP assembly that results in multiple SEC peaks, usually three when cholate is used as the detergent, that are of different molecular weight and are able to contain more specific amounts and particular membrane proteins of interest.

Figure 1A:
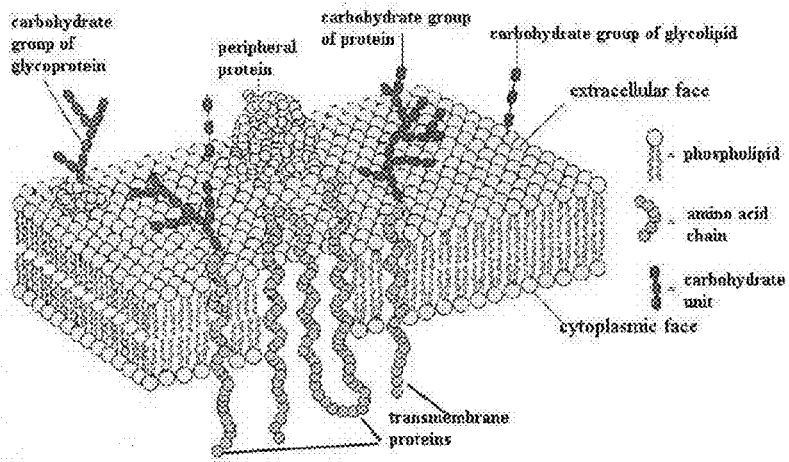
FIGS. 1A-1B show a schematic representation of methods and systems herein disclosed according to some embodiments herein disclosed and where appropriate, referred to as in situ formation.
Figure 1A:
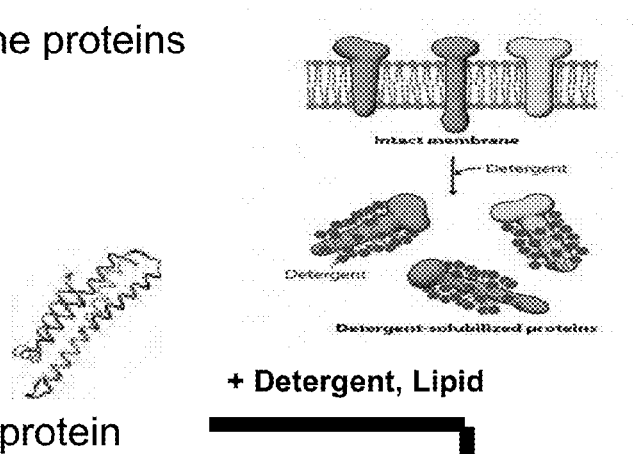
Figure 1A:
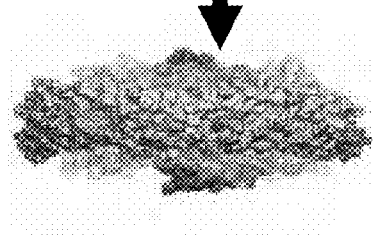

The term "solubilize" as used herein indicates to make susceptible or more susceptible to dissolve in a medium and in particular in an aqueous medium. Accordingly, when used with reference to a membrane associated protein the term solubilize indicates making the membrane associated protein soluble or more soluble (susceptible of being dissolved) into a an aqueous environment and encompasses solubilizing proteins from a pellet, a solution, a membrane fraction and any other medium and/or preparations wherein the membrane associated protein is comprised alone or in combination with other compounds and/or molecules.

The term "purify" as used herein indicate the process of freeing something from something. In particular with reference to a membrane associated protein, the term "purify" indicates the act of separating the membrane associated protein from a medium wherein the protein is comprised together with other molecules, and encompasses purification of membrane associated proteins from molecular and/or biological structures such as membranes or molecular complexes. Accordingly, "purifying" a membrane associated protein into a nanolipoprotein particle indicates the act of separating the membrane associated protein from an original environment into the nanolipoprotein particle.

The term "nanolipoprotein particle" 'nanodisc" "rHDL" or "NLP" as used herein indicates a supramolecular complex formed by a membrane forming lipid and a scaffold protein, that following assembly in presence of a target protein also include the target protein. The scaffold protein and target protein constitute protein components of the NLP. The membrane forming lipid constitutes a lipid component of the NLP.

The term "protein" as used herein indicates a polypeptide with a particular secondary and tertiary structure that can participate in, but not limited to, interactions with other biomolecules including other proteins, DNA, RNA, lipids, metabolites, hormones, chemokines, and small molecules.

The term "polypeptide" as used herein indicates an organic polymer composed of two or more amino acid monomers and/or analogs thereof. Accordingly, the term "polypeptide" includes amino acid polymers of any length including full length proteins and peptides, as well as analogs and fragments thereof. A polypeptide of three or more amino acids can be a protein oligomer or oligopeptide.

As used herein the term "amino acid", "amino acidic monomer", or "amino acid residue" refers to any of the twenty naturally occurring amino acids including synthetic amino acids with unnatural side chains and including both D and L optical isomers. The term "amino acid analog" refers to an amino acid in which one or more individual atoms have been replaced, either with a different atom, isotope, or with a different functional group but is otherwise identical to its natural amino acid analog.

The term "scaffold protein" as used herein indicates any protein that is capable of self assembly with an amphipatic lipid in an aqueous environment, organizing the amphipatic lipid into a bilayer, and include but are not limited to apolipoproteins, lipophorines, derivatives thereof (such as truncated and tandemly arrayed sequences) and fragments thereof (e.g. peptides), such as apolipoprotein E4, 22K fragment, liphorin III, apolipoprotein A-1 and the like. In particular, in some embodiments rationally designed amphipathic peptides can serve as a protein component of the NLP.

In some embodiments, the peptides are amphipatic helical peptides that mimic the alpha helices of an apolipoprotein component that are oriented with the long axis perpendicular to the fatty acyl chains of the amphipatic lipid and in particular of the phospholipid.

The wording "membrane associated protein" or "target protein" as used herein indicates any protein having a structure that is suitable for attachment to or association with a biological membrane or biomembrane (i.e. an enclosing or separating amphipathic layer that acts as a barrier within or around a cell). In particular, target proteins include proteins that contain large regions or structural domains that are hydrophobic (the regions that are embedded in or bound to the membrane); those proteins can be extremely difficult to work with in aqueous systems, since when removed from their normal lipid bilayer environment those proteins tend to aggregate and become insoluble. Accordingly, target proteins are protein that typically can assume an active form wherein the target protein exhibits one or more functions or activities, and an inactive form wherein the target protein doe not exhibit those functions/activities. Exemplary target proteins include but are not limited to membrane proteins, i.e. proteins that can be attached to, or associated with the membrane of a cell or an organelle, such as integral membrane proteins (i.e. proteins (or assembly of proteins) that are permanently attached to the biological membrane.), or peripheral membrane proteins (i.e. proteins that adhere only temporarily to the biological membrane with which they are associated). Integral membrane proteins can be separated from the biological membranes only using detergents, nonpolar solvents, or sometimes denaturing agents. Peripheral membrane proteins are proteins that attach to integral membrane proteins, or penetrate the peripheral regions of the lipid bilayer with an attachment that is reversible.

The term "membrane forming lipid" or "amphipatic lipid" as used herein indicates a lipid possessing both hydrophilic and hydrophobic properties that in an aqueous environment assemble in a lipid bilayer structure that consists of two opposing layers of amphipathic molecules known as polar lipids. Each polar lipid has a hydrophilic moiety, i.e., a polar group such as, a derivatized phosphate or a saccharide group, and a hydrophobic moiety, i.e., a long hydrocarbon chain. Exemplary polar lipids include phospholipids, sphingolipids, glycolipids, ether lipids, sterols and alkylphosphocholins. Amphipatic lipids include but are not limited to membrane lipids, i.e. amphipatic lipids that are constituents of a biological membrane, such as phospholipids like dimyrisoylphosphatidylcholine (DMPC) or Dioleoylphosphoethanolamine (DOPE) or dioleoylphosphatidylcholine (DOPC). The membrane forming lipid can assume different states in an aqueous environment, including a frozen gel state (here also gel state) and a fluid liquid-crystalline state (here also crystalline state) (Silvius J R 1982), wherein each state is associated with one or more temperatures at which the particular structural phase is detectable (Cullis P R 1991). Therefore each membrane forming lipid has a gel temperature that comprises all the temperatures at which the gel state can be detected and a crystalline temperature that comprises all the temperatures at which the crystalline state can be detected. Additionally, since a membrane forming lipid can transition from a state to another on the basis of the temperature each membrane forming lipid has also a gel-crystalline transition temperature ($T_c$) which is the temperature at which this transition occurs. State temperatures and transition temperatures of various membrane forming lipids can be found by monitoring modifications of the state of the lipid while modifying the temperature of the lipid. Techniques to monitor transitions of states of a lipid are identifiable by a skilled person and include, but are not limited to, dual polarization interferometry (DPI), nuclear magnetic resonance (NMR), Electron Spin Resonance (ESR), fluorescence and differential scanning calorimetry (DSC).

The term "detect" or "detection" as used herein indicates the determination of the existence, presence or fact of an molecule, such as a membrane forming lipid or a target protein and/or related activities in a limited portion of space, including but not limited to a sample, a reaction mixture, a molecular complex and a substrate. A detection is "quantitative" when it refers, relates to, or involves the measurement of quantity or amount of the a membrane forming lipid or a target protein and/or related activities (also referred as quantitation), which includes but is not limited to any analysis designed to determine the amounts or proportions of a membrane forming lipid or a target protein and/or related activities. A detection is "qualitative" when it refers, relates to, or involves identification of a quality or kind of the a membrane forming lipid or a target protein and/or related activities in terms of relative abundance to another a membrane forming lipid or a target protein and/or related activities, which is not quantified.

The membrane forming lipid and the protein components of the NLP are generally able to self-assemble in a biological (largely aqueous) environment according to the thermodynamics associated with water exclusion (increasing entropy) during hydrophobic association.

In the methods and systems herein provided, the amphipatic lipid and the protein components of the NLP are initially contacted to form an admixture. The term "admixture" or "mixture' as used herein indicates a product of mixing the above mentioned components, which in particular can be performed by adding those components in the mixture.

Figure 1B:
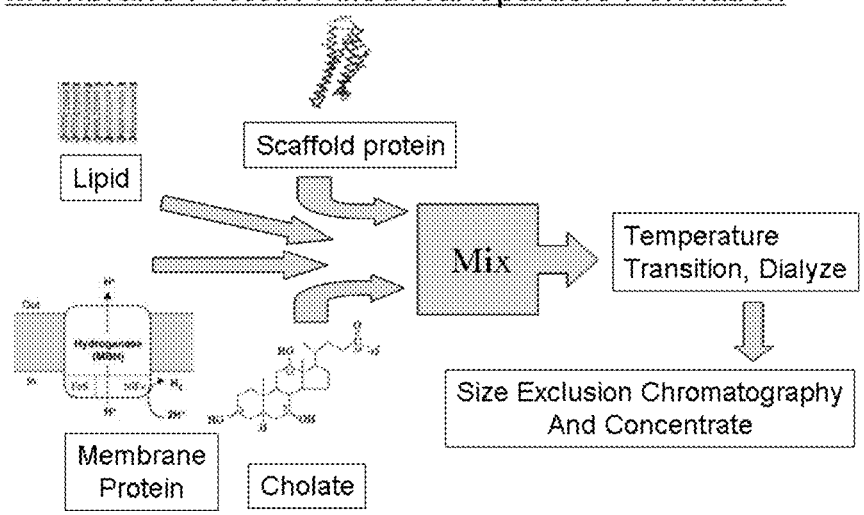
Figure 2:
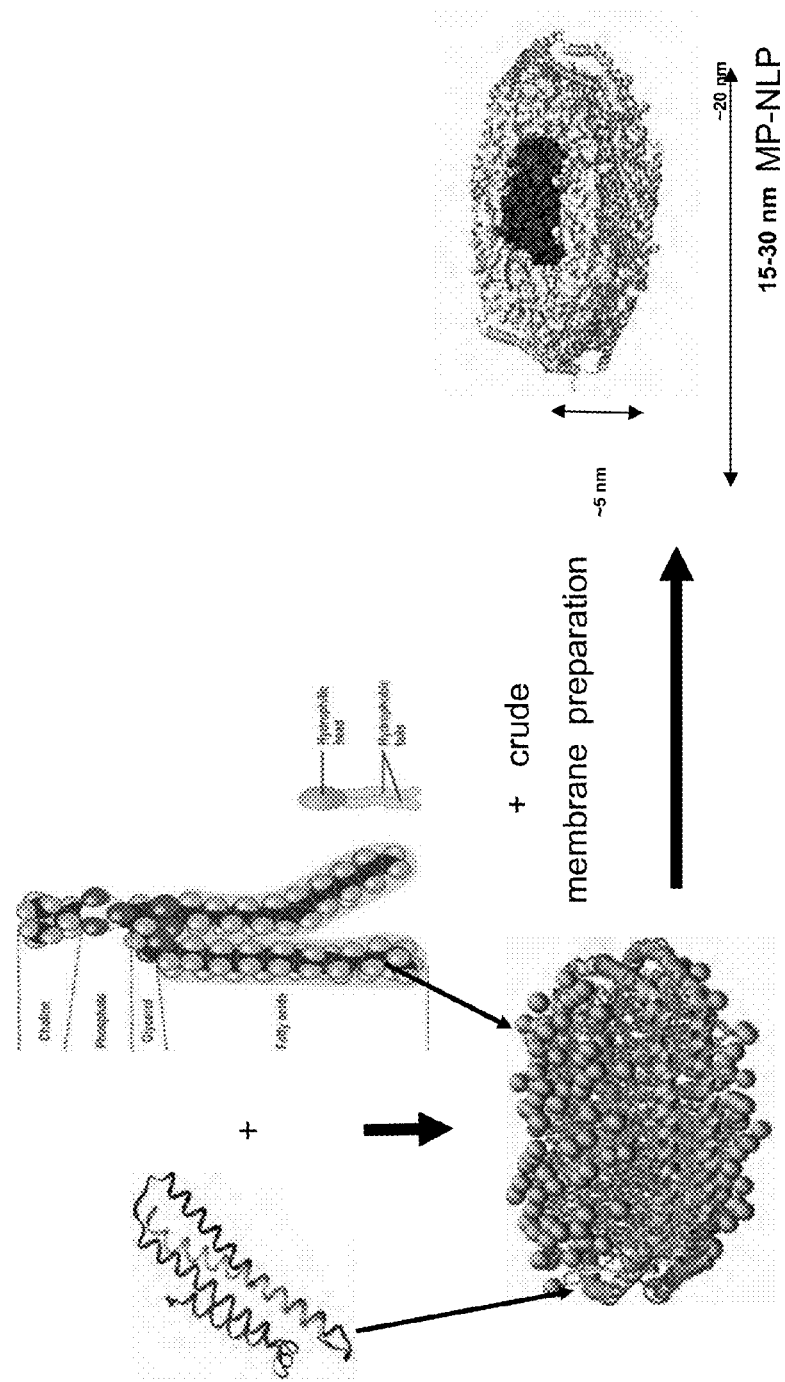
FIG. 2 shows a schematic representation of methods and systems herein disclosed according to an embodiment herein disclosed, and where appropriate, referred to as ex situ formation or intercalation.

In particular, contacting the membrane associated protein with the scaffold protein and the membrane forming lipid can be performed according to the approaches schematically illustrated in FIGS. 1A, 1B and 2. In particular, according to the approaches of FIG. 1A and FIG. 1B the membrane associated protein are contacted with the other NLP components in the mixture to form an NLP including the membrane associated protein. In particular, in the approach of FIG. 1B, the membrane associated protein is pretreated to form a protein/detergent complex that is then contacted with the other NLPs components. The approaches of FIG. 1A or 1B is also indicated as in situ formation of NLPs or in situ approach. In some embodiments, of the in situ approaches the membrane forming lipid can be pre-treated with sonication or detergent solubilization to enable the membrane forming lipid to be soluble and improve the interaction of the lipids and the proteins in the admixture. In the approaches illustrated in FIG. 2, instead the NLP is first formed by any method identifiable by a skilled person or is provided pre-formed, and then contacted with the membrane associated protein using the methods described herein, referred to as ex situ formation or intercalation.

In all the approaches the target protein can be provided in various forms including but not limited to target proteins in a solubilized form (e.g. from a membrane), target proteins comprised in a cell membrane, target proteins comprised in a membrane preparation, and target proteins in other forms identifiable by a skilled person upon reading of the present disclosure.

In particular, in embodiments where solubilization and/or purification of the target protein is desired the target protein can be provided in membranes or membrane preparations, including but not limited to cell membranes and crude membrane extracts. In particular, in embodiments wherein analysis of a target protein from an existing membrane environment is desired, the processing of the membrane environment should be minimized up to contacting the target protein present in a living cell.

In particular, in some embodiments, providing the target protein is performed by providing said protein in a crude cell pellets or membrane fraction. These crude preparations can be obtained through a variety of methods. Such methods can include simple cell lysis and centrifugation or more elaborate techniques that involve density gradients or multiple steps of fractionation.

The wording "crude cell pellets" as used herein indicates samples that contain cellular material that has been lysed through a variety of techniques and then separated from soluble material using centrifugation.

The wording "membrane fraction" as used herein indicates material obtained from crude cell pellets that contain both membrane proteins and membrane lipids, separated from soluble protein and other cellular components.

In some embodiments, the membrane fractions are crude membrane fractions outer or inner membrane fractions from gram-negative bacteria such as *Y. pestis* outer and inner membrane fractions as exemplified in Examples 1 to 6.

In some embodiments, the membrane forming lipid can be contacted with the membrane associated protein and the scaffold protein at a temperature above the membrane forming lipid gel-crystalline transition temperature.

In the methods herein described the NLP components are contacted in proportions that are functional to the number and/or size of the membrane associated protein to be included in the NLP and are identifiable by a skilled person upon reading of the present disclosure. The appropriate membrane associated protein:lipid ratio is functional to the formation of nanometer-sized, discoidal, particles containing a thermal stable outer scaffold of protein and an inner bilayer membrane mimetic made of lipid molecules that can appropriately accommodate membrane proteins in their midst and can be identified by several methods including protein assays and phospholipid content assays (for example see North P. and Fleischer S. 1983), immunogold cryo-electron microscopy, or STEM-PIXE could all be used to determine the protein lipid ratio. Additionally, the appropriate membrane associated protein:lipid ratio is functional to a complex that does not cause non-functional aggregation of either protein scaffold or membrane protein and one that enables the specific interaction of these components within the entity known as a nanolipoprotein particle, the size and number of the protein to be assembled and usually range from about 6:1 in term of mass for large and/or numerous target proteins and in particular multiple target proteins in a single fraction to about 4:1 for NLPs including multiple target proteins in multiple fractions to even lower ratio for NLP including target protein of small dimensions in single or multiple fractions. Additional ratios among the NLP components that are functional to the desired NLP to be assembled are identifiable by the skilled person and will not be further discussed in details.

Additional components of the admixture are identifiable by a skilled person upon reading of the present disclosure.

In the methods and systems herein provided, once the admixture is formed the amphipatic lipid and the protein components of the NLP are allowed to assemble for a time and under conditions that include subjecting the admixture to a temperature transition cycle in presence of a detergent.

The wording "temperature transition cycle" as used herein indicates a sequence of a temperature increase step and temperature decrease step, wherein the cycle comprises at least one temperature increase step and at least one temperature decrease step. In the temperature transition cycle of the methods herein disclosed, the temperature increase step can precede or follow the temperature decrease step.

In particular, in the temperature increase step of the cycle the admixture is brought to a temperature above the gel-crystalline transition temperature of the membrane forming lipid present in the admixture and selected as a component of the nanolipoprotein particle to be formed. In particular, in the temperature increase step the admixture can be brought to any of the crystalline temperatures of the membrane forming lipid (i.e. any temperature at which the lipid is detectable in a crystalline state). On the other hand, in the temperature decrease step of the cycle, the admixture is brought to a temperature below the gel-crystalline transition temperature of the membrane forming lipid present in the admixture and selected as a component of the nanolipoprotein particle to be formed. In particular, the temperature decrease step, the admixture can be brought to any of the gel temperatures of the membrane forming lipid (i.e. any temperature at which the lipid is detectable in a gel state).

The difference in temperature of the temperature increase step can be the same or different than the difference in temperature of the temperature decrease step and in several embodiments is from about a 24° C. difference in temperature to about 30° difference in temperature.

In the temperature cycle the duration of each step is usually such that at least a fraction, and preferably the majority, of the membrane forming lipid molecules in the mixture change its state. For example, in some embodiments, each step could be performed for about 10 min.

In the methods herein disclosed the admixture has to be subjected to at least one temperature transition cycle. In several embodiments, wherein maximization of the formation of nanolipoprotein particles is desired, the number of temperature transition cycle is increased and the admixture is preferably subjected to multiple transition cycles, which in some embodiments include at least three temperature cycles, in other embodiments include multiple temperature transition cycles performed on the admixture overnight or even a higher number.

In several embodiments, the admixture can be mixed before subjecting the admixture to the temperature transition cycle. In several embodiments the admixture can also be heated to a crystalline temperature, before subjecting the admixture to the temperature transition cycle. This type of lipid pre-treatment may enhance MP-NLP assembly by correcting improperly phased lipid or by eliminating lipid that will not properly associate due to stability, and can be replaced by additional lipid molecules to maintain an appropriate mass ratio.

An exemplary procedure to perform the temperature transition cycle includes placing the protein-lipid-detergent mixture into a temperature regulated water bath that is below or above the transition temperature of the bulk lipid followed by a water bath that is the opposite of the first water bath relative to the transition temperature. Additional exemplary procedures are illustrated in the examples.

In the methods, the temperature transition cycle is performed in presence of a detergent. The term "detergent" as used herein indicates a surfactant i.e. a wetting agent that lower the surface tension of a liquid, and in particular water, allowing easier spreading, and lower the interfacial tension between two liquids. Detergents include but are not limited to any substance improving fluidity of the membrane forming lipid and solubilization of the membrane associated protein such as cholate or other ionic or non-ionic surfactants.

The wording "in presence" as used herein with reference to the detergent indicates the fact or condition of that detergent of being present in that admixture, which includes but is not limited to presence following addition to the mixture performed.

In several embodiments, the temperature transition cycle is followed by an incubation step which is performed by bringing the admixture at the temperature transition of the membrane lipid of choice for a predetermined amount of time that is functional to a desired amount of assembled nanolipoprotein particles. For example, in embodiments, wherein the amount of assembled nanolipoprotein particle is maximized the incubation time is also increased. In some embodiments, the incubation step can be performed on the admixture for about 20-24 hr.

In several embodiments, the detergent is removed from the mixture following the temperature transition cycle and the optional incubation. This step is in particular desirable in embodiments wherein stability and/or a reduced variability of the formed NLPs is desired. Removal of the detergent can be performed according to methods that are identifiable by a skilled person and which include dialysis of the detergent from the mixture filtration, dialysis, or other techniques to remove excess detergent, such as bio-beads.

In several embodiments the average yields of the method is between 50 and 70%. The yield was determined by protein assay (Bradford) for the specified membrane protein relative to the empty NLP formulation.

In several embodiments, the admixture is formed due to the gel-liquid-crystalline phase transition of the membrane forming lipid to enhance the contact between the target protein, the membrane forming lipids and the scaffold protein. The admixture is then subjected to a temperature transition cycle in presence of a detergent, for a time and under condition to allow assembly of the nanolipoprotein particle. In the method, the temperature transition cycle comprises: a temperature increase step and a temperature decrease step. In the temperature increase step the admixture is brought to a temperature above the transition temperature forming a fluid liquid-crystalline phase enabling the membrane protein and scaffold protein to better contact the membrane forming lipid. In the temperature decrease step the admixture is brought to a temperature below the membrane forming lipid gel crystalline transition temperature, to help maintain the structure of the assembled species.

The NLP herein disclosed can be formed by lipid bilayers surrounding the membrane protein or proteins from the crude membranes and an apolipoprotein creating a water soluble structure surrounding the lipid bilayer. In some embodiments, the NLP assembled with the method herein described can include multiple target proteins and/or membrane protein complexes.

In some embodiments, the methods herein described are used to incorporate a target protein in a NLP The term "incorporate" or "capture" as used herein indicate the fact, act or condition of a molecule, in particular a membrane associated protein, that is originally comprised in a membrane environment and that following the methods herein described form part an NLP construct.

In some embodiments, the methods and systems herein disclosed can be used to capture and solubilize proteins and protein complexes directly from cell membrane preparations derived from fractionation.

In particular, in several embodiments the methods herein described can be performed from native membrane environments using nanolipoprotein particles formed in situ. These native membrane environments include cell membrane fractions including crude membrane preparations of bacteria and eukaryotic cells. The crude preparations can include the inner and outer membranes of gram-negative bacteria, single bilayer membranes of gram-positive bacteria, and plasma membranes of eukaryotic cells. The preparations can be prepared in many ways, including simple lysis and centrifugation or more elaborate separation schemes that sub-divide the membrane proteins.

In some embodiments, the methods and systems herein disclosed allow direct solubilization of native membrane proteins from both prokaryotic and eukaryotic membrane fractions by in situ NLP formation. NLP formation is accomplished by adding to a cell membrane fraction, purified apolipoprotein, phospholipid and/or a detergent/surfactant. Such NLP constructs will be useful for functional characterization of membrane proteins and membrane protein complexes. Specific membrane lipids including those from fractionated native membranes as extracted from Gram-negative and/or Gram-positive microorganisms, from plant cells, and from eukaryotic cell membranes as well as purified commercially available lipid molecules that constitute membrane forming lipids.

The methods and systems herein described further allow in several embodiments to capture solubilize and/or purify membrane protein in their functional form, thus allowing reproduction and/or further analysis of membrane proteins' activity, including membrane's protein catalytic activity. In some embodiments, the methods and systems herein disclosed allow taking a semi-purified or crude cell membrane fraction derived from classical cell homogenization/fractionation processes and selectively isolating constituent proteins of interest with retention of function. In some embodiments, the methods and systems herein disclosed provide robust nanolipoprotein particle preparation and characterization methods as a platform for physical and/or biochemical characterization of membrane proteins using nanolipoprotein particles.

Functionality of the target protein assembled in the NLP can be detected using techniques identifiable by a skilled person, such as binding experiments for receptor proteins or specific functional assays as described in the literature. Bockaert J. et al., 1997). For example, hydrogenase-containing NLPs can be tested for hydrogen production using GC/MS (as exemplified in the examples and related figures).

In some embodiments, the methods and systems herein disclosed allow incorporation of diverse membrane proteins into NLP constructs, which include but are not limited to integral membrane proteins containing transmembrane a-helices and/or 13-sheet structures, as well as, peripheral and monotopic membrane proteins, Type I, II and III cell-surface receptors and the likes. Membrane proteins that have single or multiple membrane spans can be functionally solubilized into NLPs.

In some embodiments, the methods and systems of the present disclosure enable the quick and easy purification and solubilization of functional membrane proteins from a cell membrane fractions or preparations in a single step.

Suitable applications for NLPs include various biological fields wherein detection of microorganisms and/or analysis of the microorganism is desired since host interactions are mediated through cell surface membrane proteins and are critical to detection, pathogenicity and determination of countermeasure with reference to the microorganism at issue. In particular, nanolipoprotein particles (NLPs) may serve as carriers of non-infective immunogenic proteins, e.g. H5 or N1 proteins (Avian influenza), as potential vaccine-based countermeasures. NLPs can serve as vehicles for delivery of therapeutic-based countermeasures, (Tufteland M Peptides (2007) 28:741-748 Peptides (2007) 28:741-748). Nanolipoprotein particles (NLPs) containing selected microbial (bacterial or viral) cell-surface membrane proteins will provide an opportunity to better understand the science of pathogenicity, e.g. Yop B, D, LcrV, Aile, etc. Nanolipoprotein particles (NLPs) will enable capture and presentation of cell surface protein features associated with known biothreat organisms and potentially could aid in detection of emerging biothreats.

The methods herein described can be used in several embodiments to analyze the total extent of the membrane proteins in a membrane sample, and in particular the proteome of a predetermined membrane fraction more easily and more completely than current methods. In some of those embodiments, forming the admixture and subjecting the admixture to the temperature transition cycle is performed for a time and under conditions that allow capturing the membrane proteome in the NLPs. The NLPs so obtained are then subjected to fractionation (e.g. by electrophoresis on a bidimensional gel) and analysis. A skilled person will be able to identify additional details concerning techniques suitable for analyzing membrane proteomes captured in NLPs according with methods herein described.

The methods herein described can be used in several embodiments to analyze protein-protein interactions. In some of those embodiments, a target protein of interest is capture on an NLP and contacted with one or more candidate proteins under appropriate conditions. Occurrence of interactions can then be detected with techniques identifiable by a skilled person. Various approaches and techniques to analyze the interactions between a membrane associated protein captured in a NLP according to the methods herein disclosed and one or more candidate proteins can be identified by a skilled person and will not be further described in details.

Further details concerning the methods and systems herein disclosed, can be identified by the person skilled in the art upon reading of the present disclosure.

EXAMPLES

The methods and system herein disclosed are further illustrated in the following examples, which are provided by way of illustration and are not intended to be limiting.

In particular, in the following examples, membrane protein incorporation into nanolipoprotein particles (NLPs) is exemplified with reference to membrane proteins from a variety of sources using a variety of methods for crude membrane preparations. Applicants have incorporated outer and inner membrane proteins from bacteria (*Y. pestis* and *Acinetobacter Baumannii* respectively) membrane proteins from human red blood cells (RBC membrane) and thermococci (*P. Furiosus*). The majority of the NLP assemblies used crude membrane preparations with lipoprotein E4 N-terminal 22k fragment scaffold and DMPC lipid in the presence of cholate.

The following materials and methods were used to perform the experiments illustrated in the examples.

Phospholipid
1,2-Dimyristoyl-sn-Glycero-3-Phosphocholine
(DMPC)

DMPC was purchased from Avanti Polar Lipids, Inc. (Alabaster, Ala.). Although this lipid was the only one used for incorporation in these examples, other lipids, namely POPC, etc. can also be used. Fluorescent lipids have also been used for bR (1% DMPE (NBD-DMPE and RhoB-DMPE) and 10% DMPE and 1% NBD-DMPC).

apoE422k Protein Production:

The expression clone to produce apoE422k, the N-terminal 22 kDa fragment of apolipoprotein E4 (apoE4), as a 6H is and thyrodoxin tagged construct was kindly provided by Dr. Karl Weisgraber. Production and purification of apoE422k has been described in detail elsewhere [(Chromy B et al., 2007]. Although this protein was the only one used for scaffold in these examples, other proteins can be used. such as apoA, lipophorins, and other amphipathic lipid-binding proteins.

Membrane Fractionation (Outer and Inner Membrane Preparations from Gram-Negative Bacteria:

The gram-negative bacteria strain is grown from glycerol stocks on blood agar plates with appropriate antibiotics. (e.g., Yp 1283=50 µg/ml Streptomycin). Incubate at 26° c. for ±48 hrs. A swath of colonies is then inoculated in 25 ml of BHI/Str broth (125 ml flask) and the resulting inoculated broth is grown overnight in a water bath at 26° c. with shaking at 225 RPM. Membrane preparations that are different in amount will cause different levels of captured membrane proteins.

The overnight culture is split evenly into 2 small Oakridge tubes and the tubes are spun at 10 K RPM for 10 min at 4° c. The supernatant is discarded and the pellet is frozen at −20° c. or −80° c. The cells are lysed and each (12.5 ml culture) frozen pellet re-suspended in 1.5 ml of B-PER II solution in the hood. Vortex until suspended (usually about 1 minute). 2-10 µl of DNaseI are added per each ml of extract. The resulting mixture is gently mixed in a water bath at 37 c for 20-30 min. (Look for reduced viscosity before proceeding).

Each suspension is then transferred to a 2 ml tube, the tube is spun for 10 min at 10K RPM at 15° c. to remove unlysed cells and the supernatant was decanted into a new tube. From this point on the samples are kept ice-cold.

The suspension is aliquoted evenly into larger ultra tubes (TLA 100.3 rotor), brought up to 3.2 ml with cold *Buffer A, and mixed by pipeting. The samples are then spun in ultracentrifuge at 50K RPM (TLA 100.3 rotor) for 1 hr at 4° c., the supernatant discarded and 2 ml of [Buffer A+2% TRITON] are added to the pellet. The pellet is resuspended by pipeting to break up the pellet and the suspension is incubated on ice for 30 minutes. The ultracentrifugation is repeated for 1 hr at 50K RPM at 4° c., the supernatant (inner membrane) is saved. The pellet is then washed to remove residual triton, the pellet orientation is marked and 1 ml of Buffer A added (pipeting around side-walls when adding buffer).

The solution is spun in ultracentrifuge for 5 min at 50K RPM (place tubes with same orientation as existing pellets), the supernatant discarded and wash and centrifugation are repeated to get rid of all residual triton. The pellet (outer membrane) is resuspended in 500 µl of Buffer A or TBS. Quantitative analysis with SDS gel is ten performed.

A viability test is then performed by plating onto blood agar; growing for 48 hr and if there is growth, filtering through 0.45 or 0.22 µm filter to sterilize and then store in −80° c. Nanodrop 280 absorbance analysis is also performed. Percentage target protein in the sample is estimated from SDS gel and the relevant value adjusted to that value for assembly.

Nanolipoprotein Particle (NLP) Formation:

MP-NLPs were assembled through a process adapted from the detergent dialysis technique [Jonas, A, et al., 1986]. The final concentration of detergent needs to be maintained above its critical micellar concentration during assembly (Bayburt Nanoletters 2002). Sodium cholate (20 mM) was prepared from a 500 mM stock solution and added to DMPC suspended in Tris buffered saline to a concentration of 34 mg/mL and probe sonicated to clarity. The solution is briefly centrifuged to remove any metal contamination from the probe. For other detergents, see FIGS. 4A-4F. Constituents are combined in the following concentrations; DMPC, 11 mM:apoE422k, 90.9 µM:bR, 49.8 µM; creating a molar ratio of 130:1:1.83 respectively, i.e. lipid (6.52 mM):scaffold protein (44 µM):membrane protein (9.6 µM):detergent (13 mM), creating a ratio of 148:1:0.2:296). The order in which constituents are combined is not necessary to maintain. However, two main techniques exist for assembling MP-NLPs shown in FIGS. 1A-1B (in situ) and FIG. 2 (intercalation). "Empty" NLPs (without membrane proteins) were assembled as described by [Chromy B., et al 2007].

NLP assembly formation started with 3 repeated sets of transition temperature incubations, where the temperature was cycled from 30° C. for 10 minutes to 20° C. for 10 minutes, with light hand mixing between incubations. Next, the reaction was incubated overnight at 23.8° C. Cholate was removed by dialysis against 1000× volume of TBS buffer with 3 changes in 24 hrs. The NLPs were purified from lipid-poor and lipid-rich complexes by size-exclusion chromatography (VP HPLC, Shimadzu) using a Superdex 200 HR 10/30 column (GE Healthcare), in TBS at a flow rate of 0.5 ml/min. The column was calibrated with four protein standards of known molecular weight and Stokes diameter that span the separation range of the column and the NLP samples. The void volume was established with Blue dextran. Fractions containing MP-NLPs were concentrated to approximately 0.1 mg/ml using molecular weight sieve filters (Vivascience) with molecular weight cutoffs of 50 kDa. Protein concentration was determined using the ADV01 protein concentration kit (Cytoskeleton, Inc.).

Fluorescent Labeling:

Cy3 and Cy2 were conjugated to the E422K scaffold and bR respectively using the Cy3/2 Ab Labeling Kit (Amersham Biosciences) and following the manufacturer's instructions. Dye:protein ratios were determined by comparing the absorbance of the protein at 280 nm and the absorbance of the CyDye at 670 nm and 532 nm respectively. In both cases, the ratios provided a 1:1 correlation, suggesting that a single CyDye molecule is present on each protein.

Native PAGE:

Equal amounts of NLP samples (0.5-2 µg) are diluted with 2× native sample buffer (Invitrogen) and loaded onto 4-20% gradient pre-made Tris-HCl gels (Invitrogen). Samples are electrophoresed for 250 V·hrs at a constant 125V. After electrophoresis, gels are incubated with Sypro Ruby for 2 hours and then destained using 10% MeOH, 7% Acetic acid. Following a brief wash with ddH$_2$O, gels are imaged using a Typhoon 9410 (GE Healthcare) at 532 nm (green laser) with a 610 nm bandpass 30 filter. Molecular weights are determined by comparing migration vs. log molecular weight of standard proteins found in the NativeMark standard (Invitrogen). The Stokes diameter of the NLPs is calculated from the known Stokes diameter of the same proteins in the standard sample.

SDS PAGE:

Protein fractions were analyzed by SDS-PAGE gels, stained with Sypro Ruby (BioRad) and fluorescently imaged with a Typhoon 9410 (GE Healthcare), as described above.

UV-Visible Spectroscopy:

UV-visible spectra were collected using 50 µL of sample in a quartz cuvette on an ultrospec 5300pro UV/Visible spectrophotometer (Amersham Biosciences) Dark adapted spectra were collected after keeping the sample wrapped in foil overnight. Light adapted spectra were collected after exposure to a full spectrum bright light for 15 min. [Wang et al].

AFM Imaging:

Atomically flat Muscovite mica disks were glued to metal substrates to secure them to the scanner of a stand-alone MFP-3D AFM (Asylum Research, Santa Barbara, Calif.). 2 uL NLP solution at a 100 ng/mL concentration was incubated for two minutes on the mica surface in imaging buffer (10 mM $MgCl_2$, 10 mM Tris-HCL, and 0.1 M NaCl, adjusted to pH 8.0) then lightly rinsed through wicking. The AFM has a closed loop in the x, y, and z axes, which improved imaging fidelity. The topographical images were obtained with oxide sharpened silicon nitride levers (MSCT, Veeco, Santa Barbara, Calif.) with a spring constant of 0.1 N/m. Images were taken in alternate contact (AC) mode, also known as tapping mode, in aqueous environment, with amplitudes below 20 nm and an amplitude setpoint at 65% tapping amplitude scan rates were below 1.5 Hz. Height, amplitude, and phase images were recorded. Phase was monitored such that biphasic images were omitted. High resolution images of 600 nm by 600 nm were acquired at 512 by 512 pixel resolution, such that each NLP on average contained 600 pixels. The density of particles on the mica substrate was kept low, on average 90 particles per 1 $um^2$, to facilitate individual particle identification and sizing. Experiments were carried out in a temperature controlled room at 23+/−1° C., with acoustic hood isolation and active vibration damping.

AFM Image Analysis:

Heights of features in images were examined by histogram analysis using IgorPro Wavemetrics software routines, where contiguous particles were defined by a threshold height above the background and the height arbitrarily defined as the maximum height contained by 10 or more pixels within the particle.

Ion Mobility Spectrometry:

IMS determines the mean aerodynamic diameter population distribution of particles in a volatile buffer. NLP samples were exchanged via dialysis into a 25 mM ammonium acetate buffer and the aerodynamic diameter of NLPs determined with a Macroion Mobility Spectrometer (Model 3890, TSI Inc., Shoreview, Minn.), as previously described (Bacher 2001). NLP aerodynamic diameters were subsequently converted to aerodynamic spherical volumes as previously described.

Example 1

Incorporation of Membrane Preparations from *Y. Pestis* in NLPs

Figure 3A:
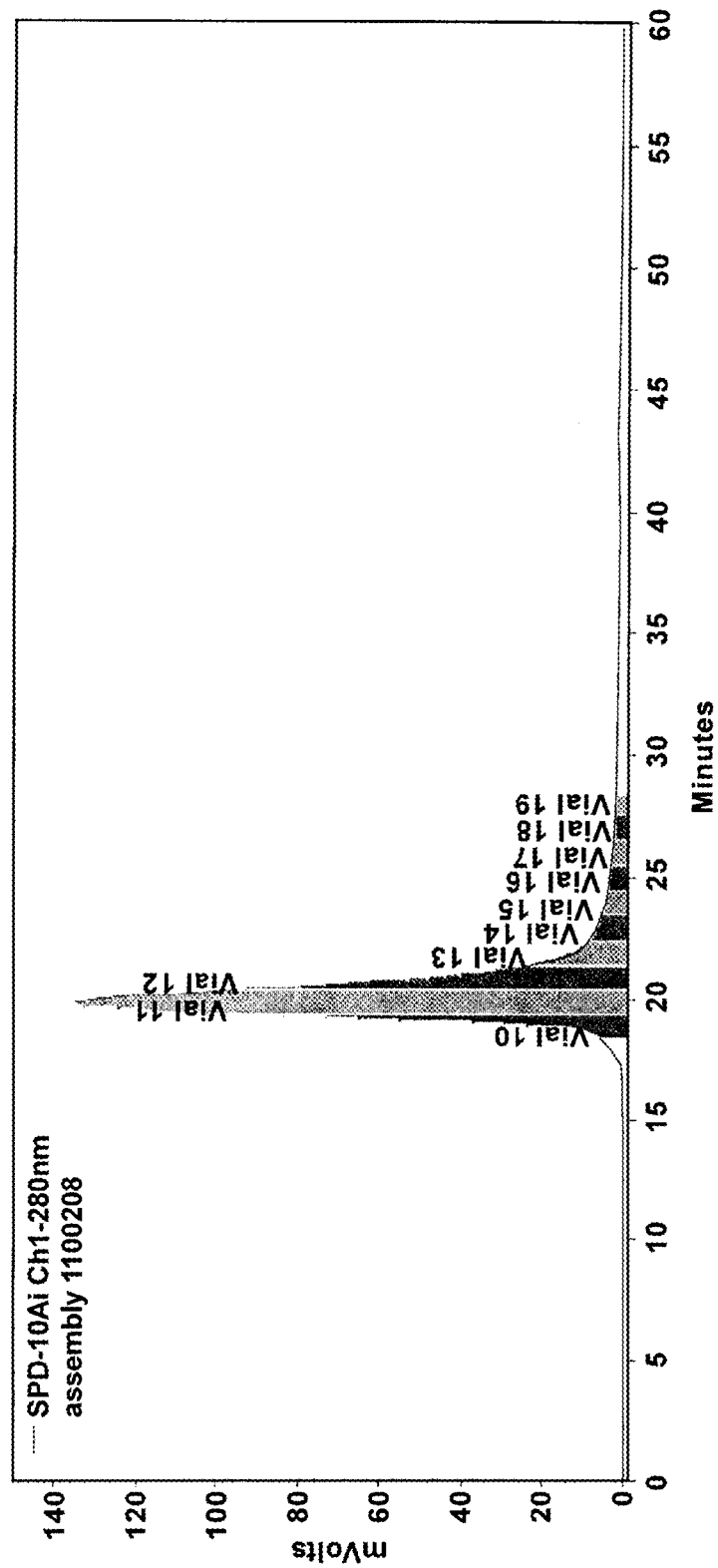
FIGS. 3A-3B show size exclusion chromatography (SEC) traces of 'empty' NLPs made using the in situ approach (as in FIGS. 1A-1B) using two different ratios of lipid to scaffold protein.
Figure 3B:
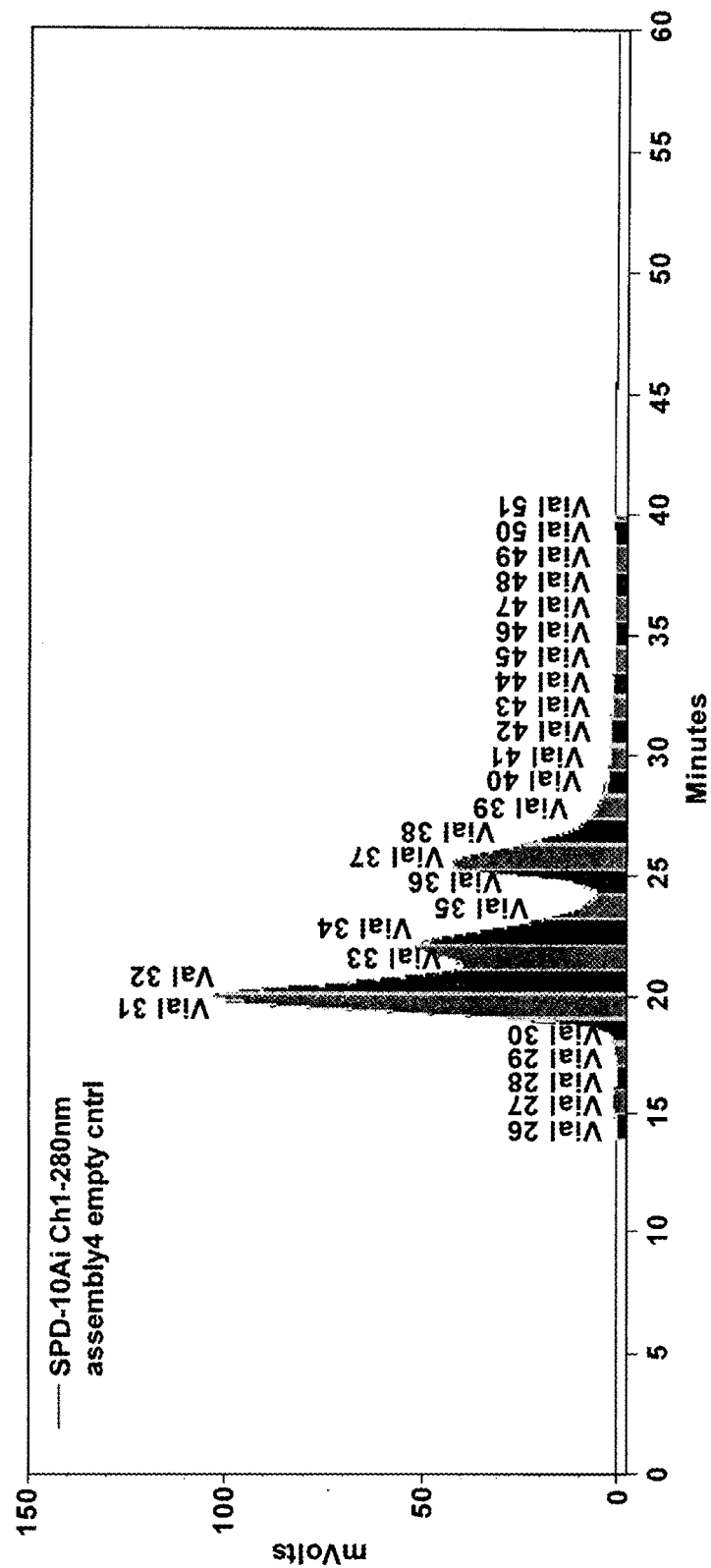
Figure 4A:
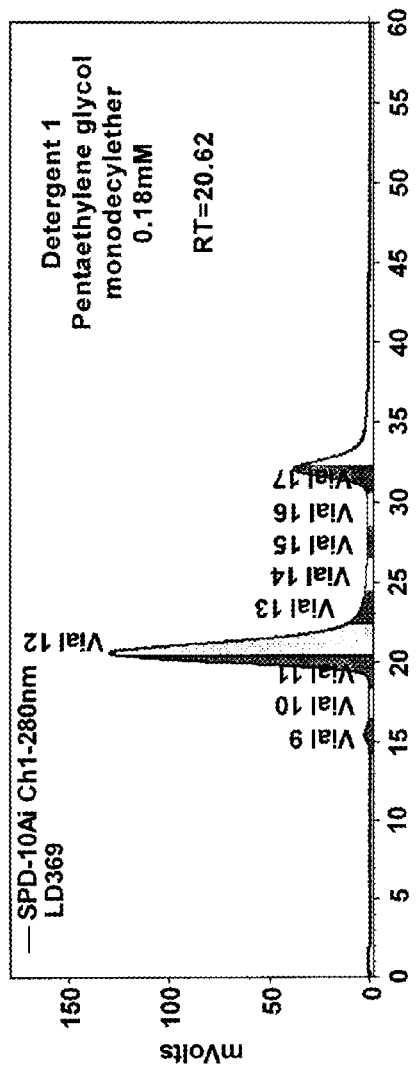
FIGS. 4A-4F show SEC traces and native gel characterization of empty NLPs made with different detergents. SEC traces of empty NLPs made using five different detergents are shown (FIGS. 4A-4E) with their corresponding native page characterization (FIG. 4F). Although a large number of potential detergents can be used for MP-NLPs, the data here show that these five particular detergents can successfully enable formation of NLPs.
Figure 4B:
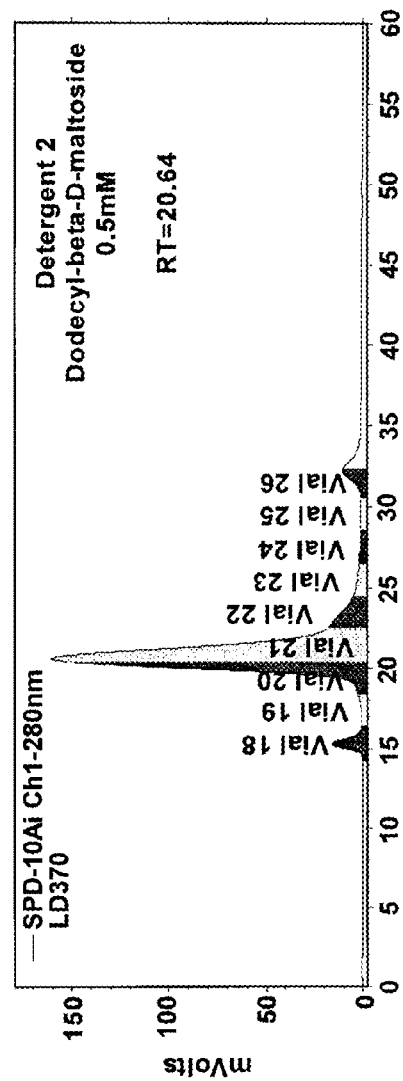
Figure 4C:
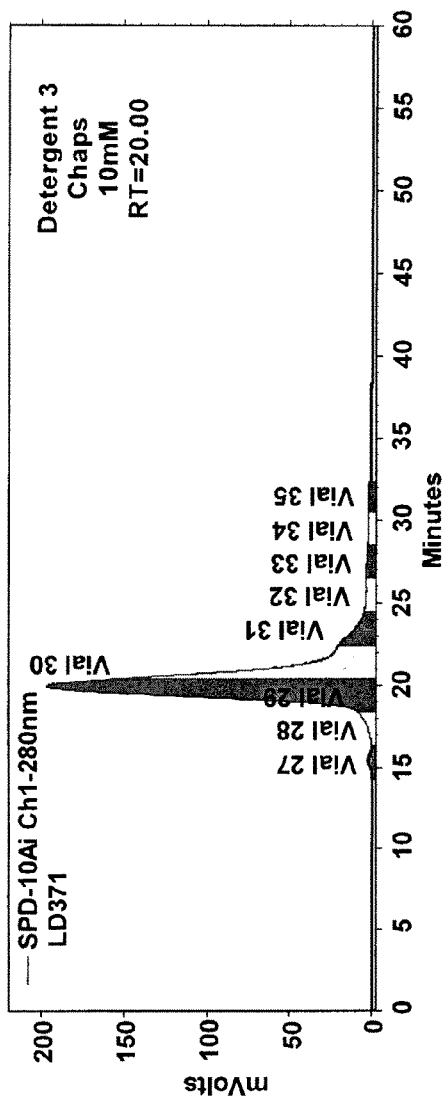
Figure 4D:
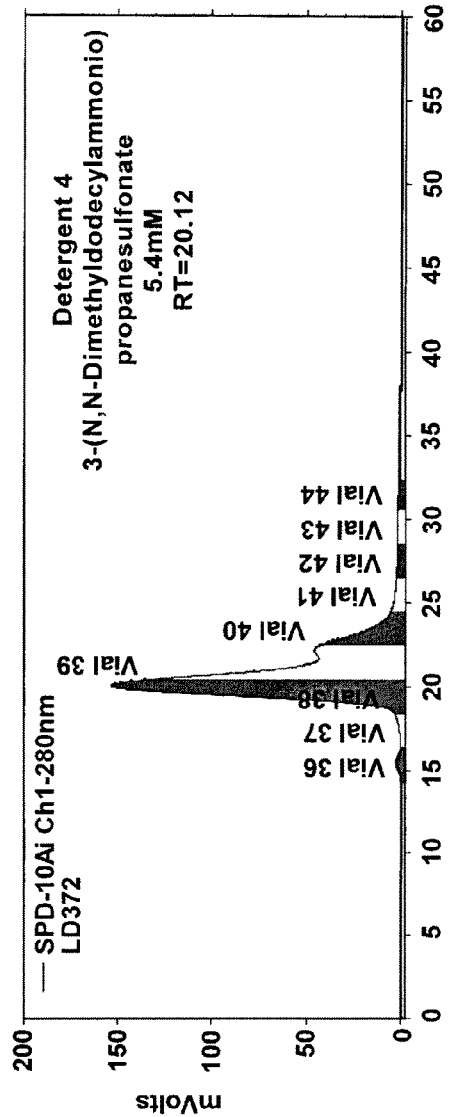
Figure 4E:
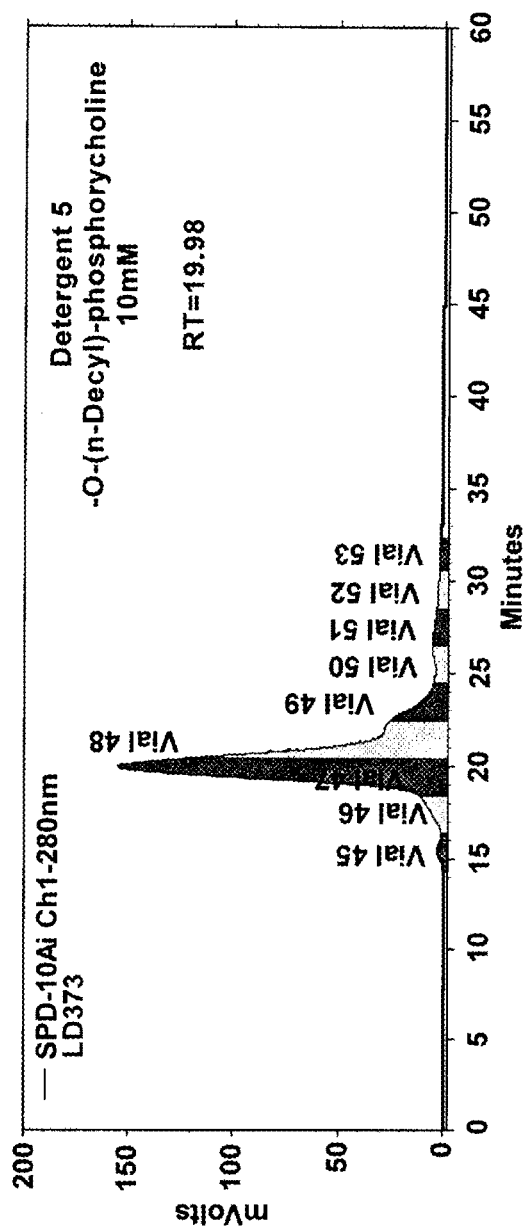
Figure 4F:
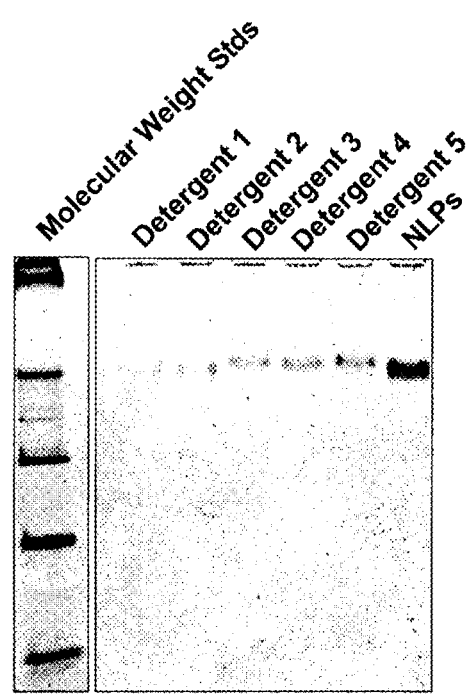
Figure 5A:
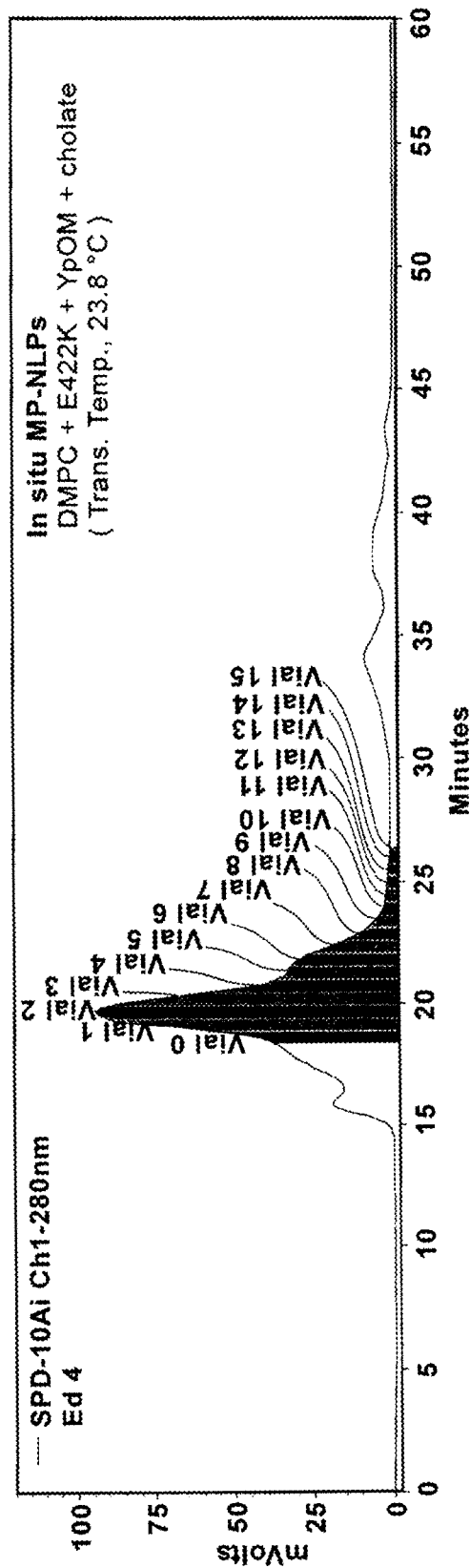
FIGS. 5A-5B show SEC traces of MP-NLPs using in situ formation as compared to the established detergent dialysis method. A higher yield of NLPs as determined by absorbance units in the MP-NLP fractions are obtained from the in situ method reported here (FIG. 5A) as compared to the detergent dialysis method (FIG. 5B).
Figure 5B:
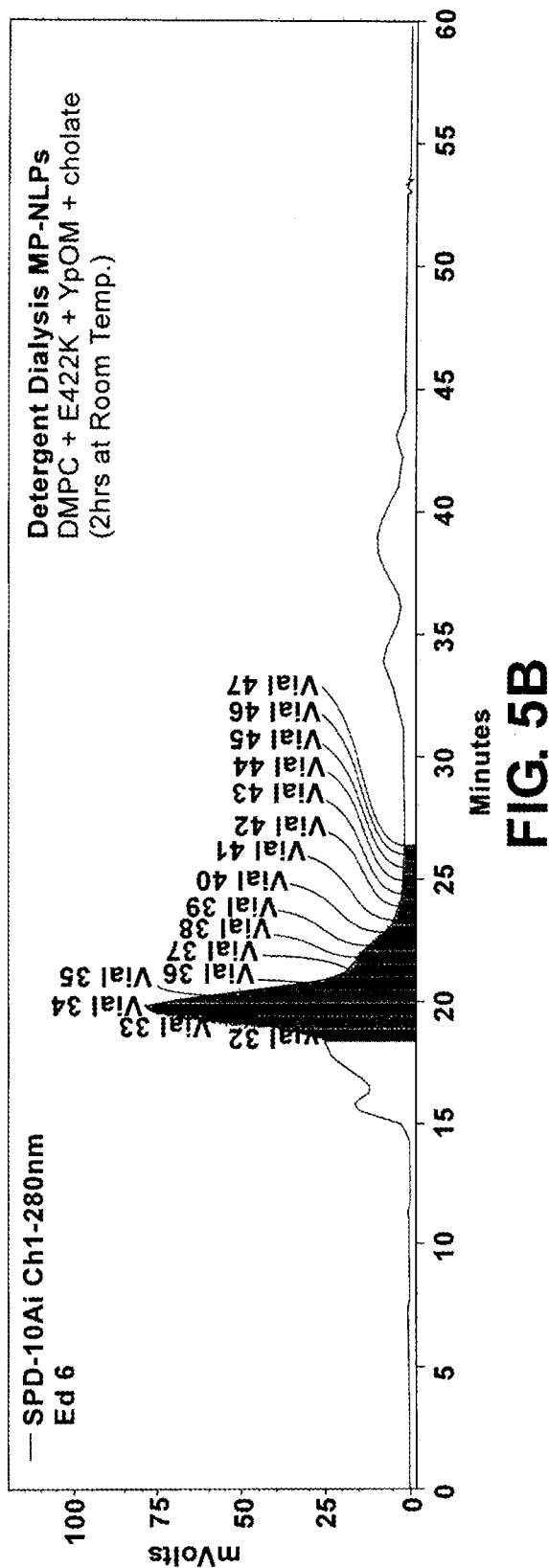
Figure 6:
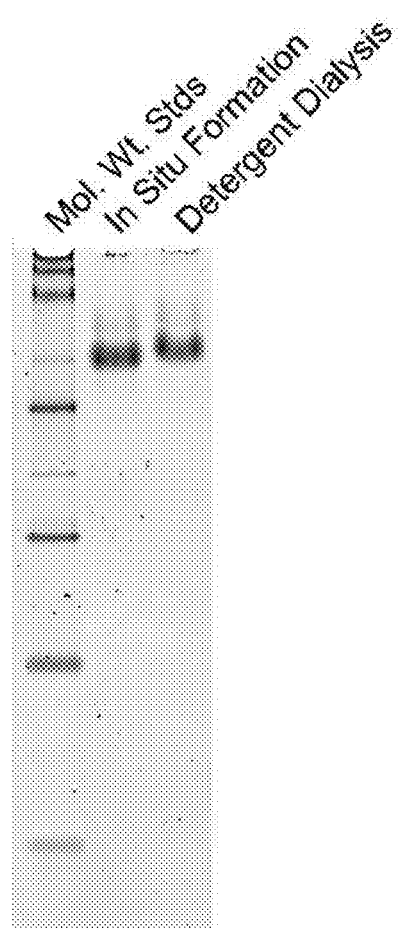
FIG. 6 shows a native gel highlighting the molecular weight and existence of NLPs in the in situ formation method as compared to the detergent dialysis method. Both preparations show a major band at ~700 kDa. These MP-NLPs show similar sized bands showing that the size and structure are consistent with nanolipoprotein particles.
Figure 7:
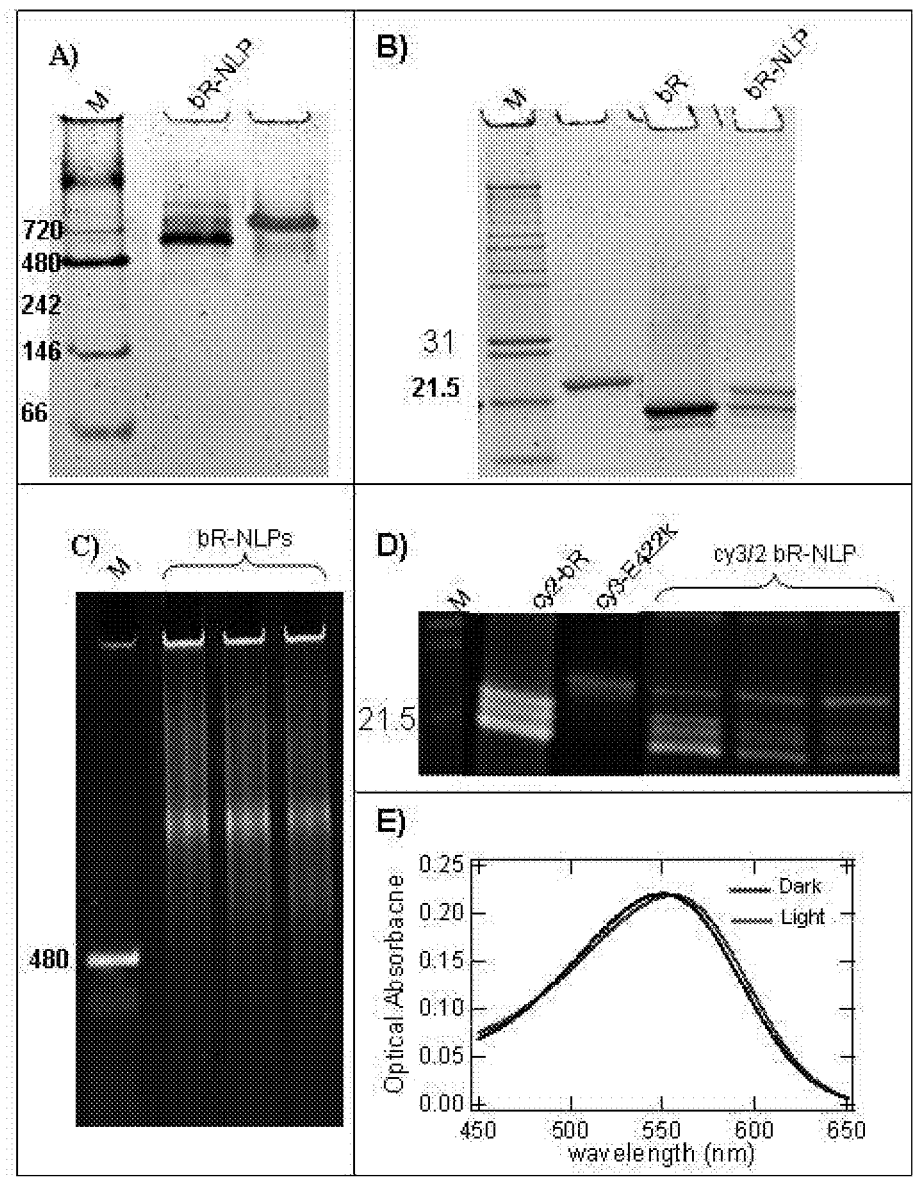
FIG. 7 shows MP-NLPs made using the in situ formation technique with a bacteriorhodopsin-containing purple membrane preparations obtained from the Haloarchaea, *Halobacterium salinarium*. Native gel, SDS PAGE and UV-visible spectroscopy of bR-NLPs. A) Native gel electrophoresis of bR-NLPs and empty-NLPs B) Tricine denaturing gel 16% SDS PAGE for an empty-NLP assembly, bR, and bR-NLP assembly. The bR-NLP lane displays two distinct bands corresponding to bR and apoE422k. C) Native gel electrophoresis of 3 SEC fractions spanning the entire NLP-rich peak for bR-NLPs assembled from cy2 labeled bR and cy3 labeled apoE422k, where green indicates cy2-E422k, red indicates cy3-bR and the yellow is the co-localization of both proteins D) Tricine denaturing gel 16% SDS PAGE of Cy2-bR, Cy3-apoE422k and 3 SEC fractions spanning the entire NLP-rich peak for bR-NLPs assembled from Cy2-bR and Cy3-apoE422k. The Cy3/Cy2 bR-NLPs contained two bands; a red band and green band indicating the presence of both cy2-bR and cy3-apoE422k. E) UV-Vis absorbance spectra showing 550.7 nm and 556.0 nm absorbance maxima for dark adapted bR-NLPs and light adapted bR NLPs respectively. Empty NLPs showed no significant absorbance at these wavelengths (not shown).

Membrane preparations from *Y. pestis* are derived according to procedure herein illustrated. In those procedures, both wild-type and mutant strains can be used. FIGS. 3A and 3B show a native gel of MP-NLPs formed using the in situ method (FIG. 2) highlighting multiple sized NLP species. NLP bands are present at more than one location on the gel. These bands represent MP-NLPs of differing size and incorporate different sets of proteins from the membrane preparations. The size exclusion chromatography traces that gave rise to the different NLP bands are shown in FIGS. 4A-4E. As can be seen by comparing the species in NLP4v25 and NLP4v28 with the SEC traces in FIGS. 4A-4E, the molecular size of these MP-NLPs can be dramatically different. The membrane proteins that these differently sized MP-NLPs can accommodate are also different.

Gram-negative bacteria are grown in sufficient quantity to produce a large amount of membrane proteins (currently we grow 50-100 ml cultures). The bacteria are harvested and centrifuged (~1 k×g) to separate cells from growth media. Cells are lysed by a number of different methods: 1. sonication, 2. trituration in chemical lysis solutions, such as B-per from Pierce. 3. bead-beated with zirconium beads, 4 lysed using pressure in a French press or in the Pressure Biosystems Inc. PCT instrument. Mammalian and yeast cells can also be lysed by homogenization. Following lysis, samples are spun down and separated from nucleic acids, cell particles and other cell debris using a low speed centrifugation (16 k×g). Soluble proteins are then separated from membrane proteins using high speed centrifugation (100 k×g). Alternatively, membrane proteins can be incorporated into NLPs directly from cell lysates.

Example 2

Large NLP—Single Peak Optimization from Cholate Formed NLP

Membrane preparations from *Y. pestis* are derived according to procedure herein illustrated. FIGS. 3A and 3B show the empty NLP that provides a single-sized NLP for eventual incorporation of membrane proteins. This method which varied the scaffold protein to lipid ratio to 1:6 on a mass ratio, highlights the ability to alter the NLP size to obtain the membrane proteins of interest.

Example 3

*Yersinia pestis* Outer Membrane Protein NLPs

Figure 14A:
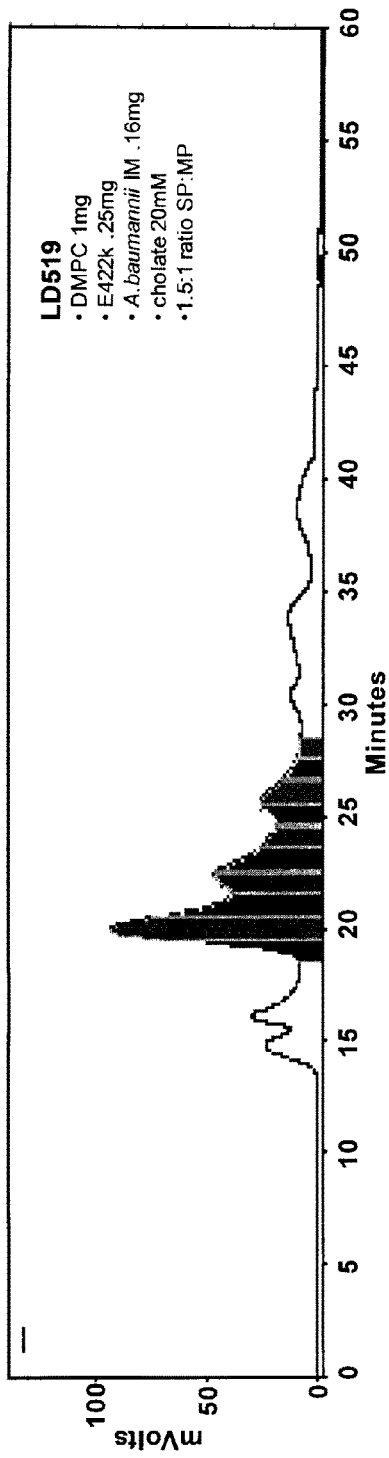
Figure 14B:
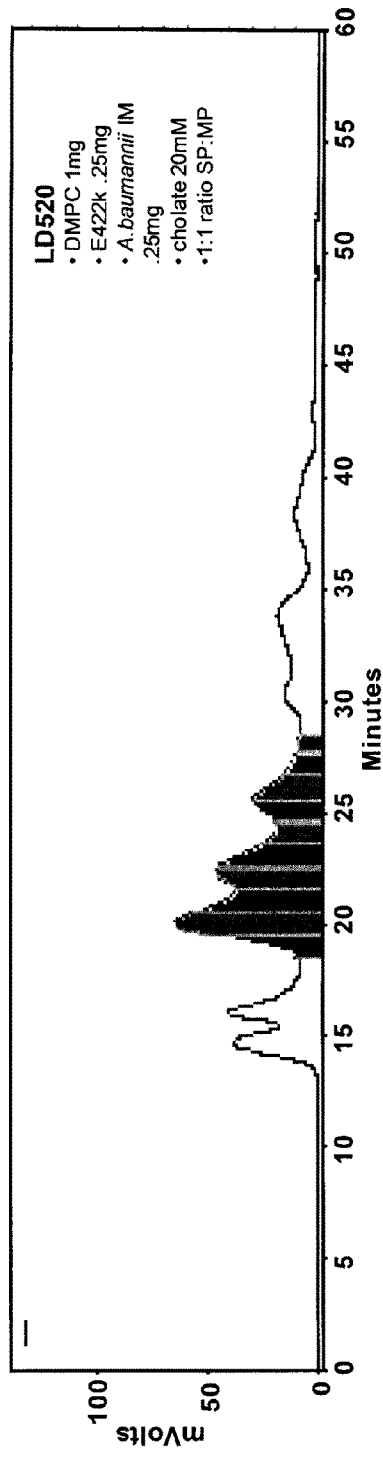
Figure 15:
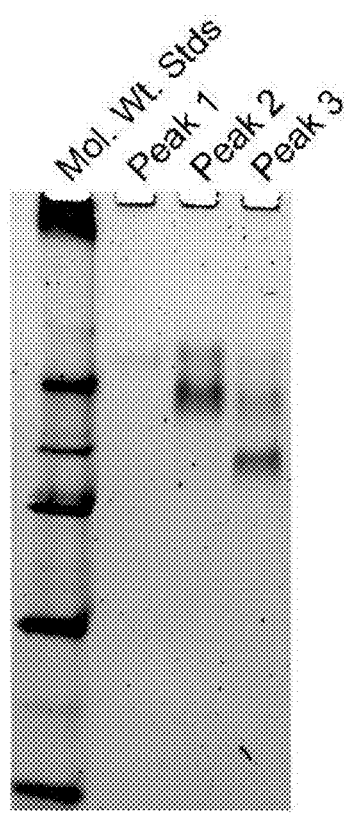
Figure 16:
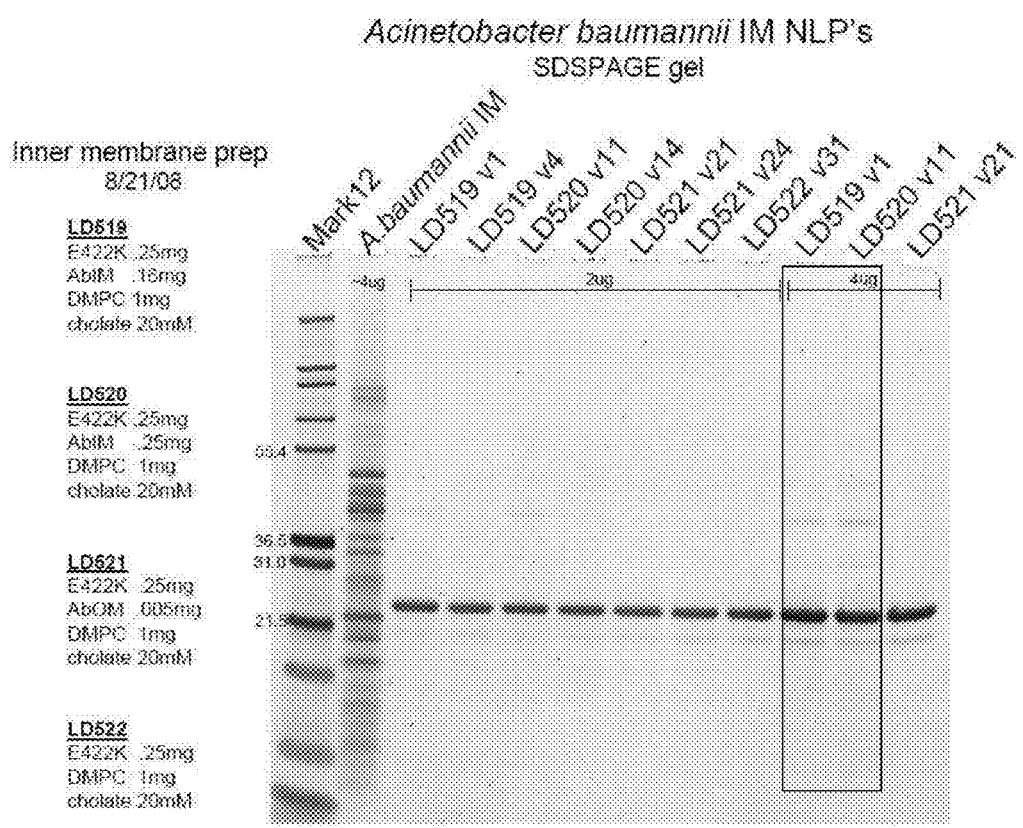
Figure 17:
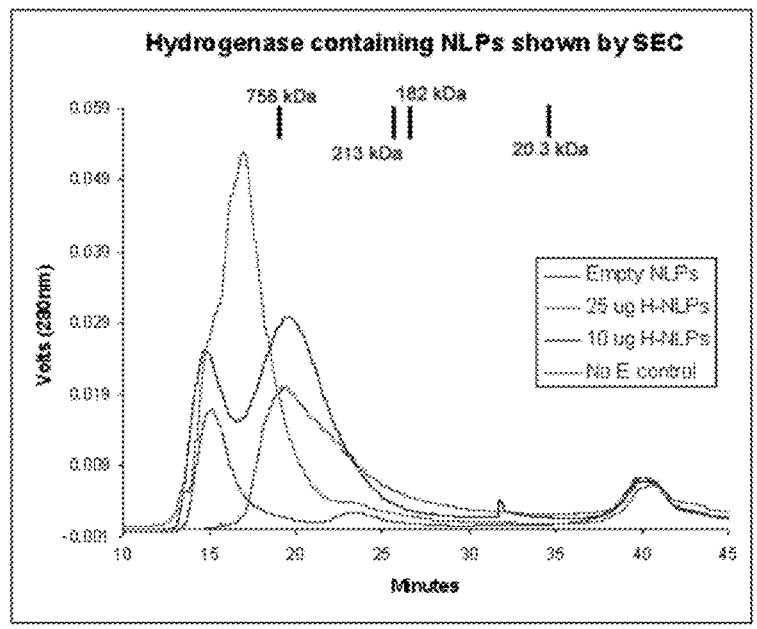
Figure 19:
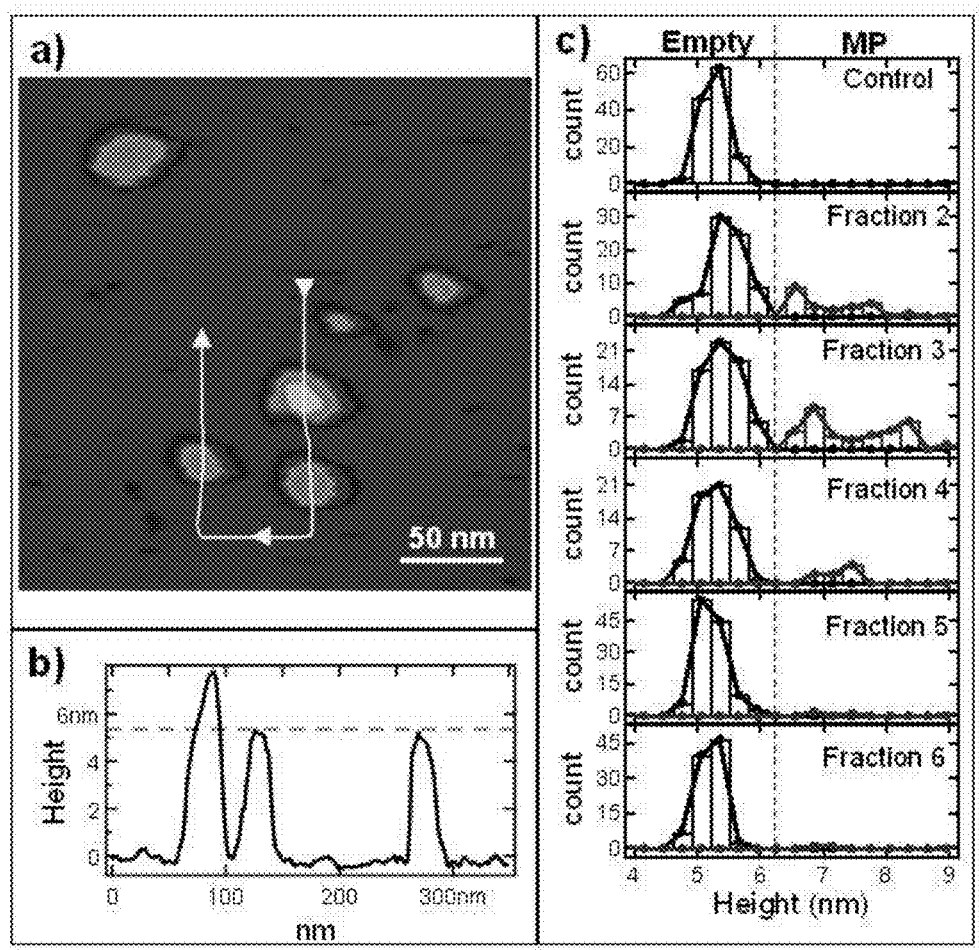

Membrane preparations from *Y. pestis*. In this embodiment, the MP-NLPs contain different NLPs based on the SEC fraction. For example, FIGS. 14-16 shows different *Y. pestis* outer membrane proteins are present in the different SEC fractions. SDS-PAGE highlights the particular protein bands that exist in the different fractions. The ratio of membrane protein to scaffold protein are 1.5:1 down to 1:1, showing similar results for these ratio levels.

Example 4

Virulence Factor AilC "Captured" Directly from *Y. pestis* Crude Membrane Fraction Direct capture of a membrane associated protein using the methods and systems of the present disclosure was performed using outer membrane (O.M.) fraction isolated from wild-type KIM D27 and AilC deletion mutant strains. In particular the OM fraction and the AilC mutant strain were used to assemble NLPs.

The cells were pelleted at 12K×g and subsequently lysed with French Press. The membranes were centrifuged at 263K×g and the outer membranes were separated from inner membranes by Triton X-100 solubilization and recentrifugation. E22K:AilC:OMPC (1:0.75:4) was then obtained in the presence of cholate (20 mM) in TSS.

Figure 8:
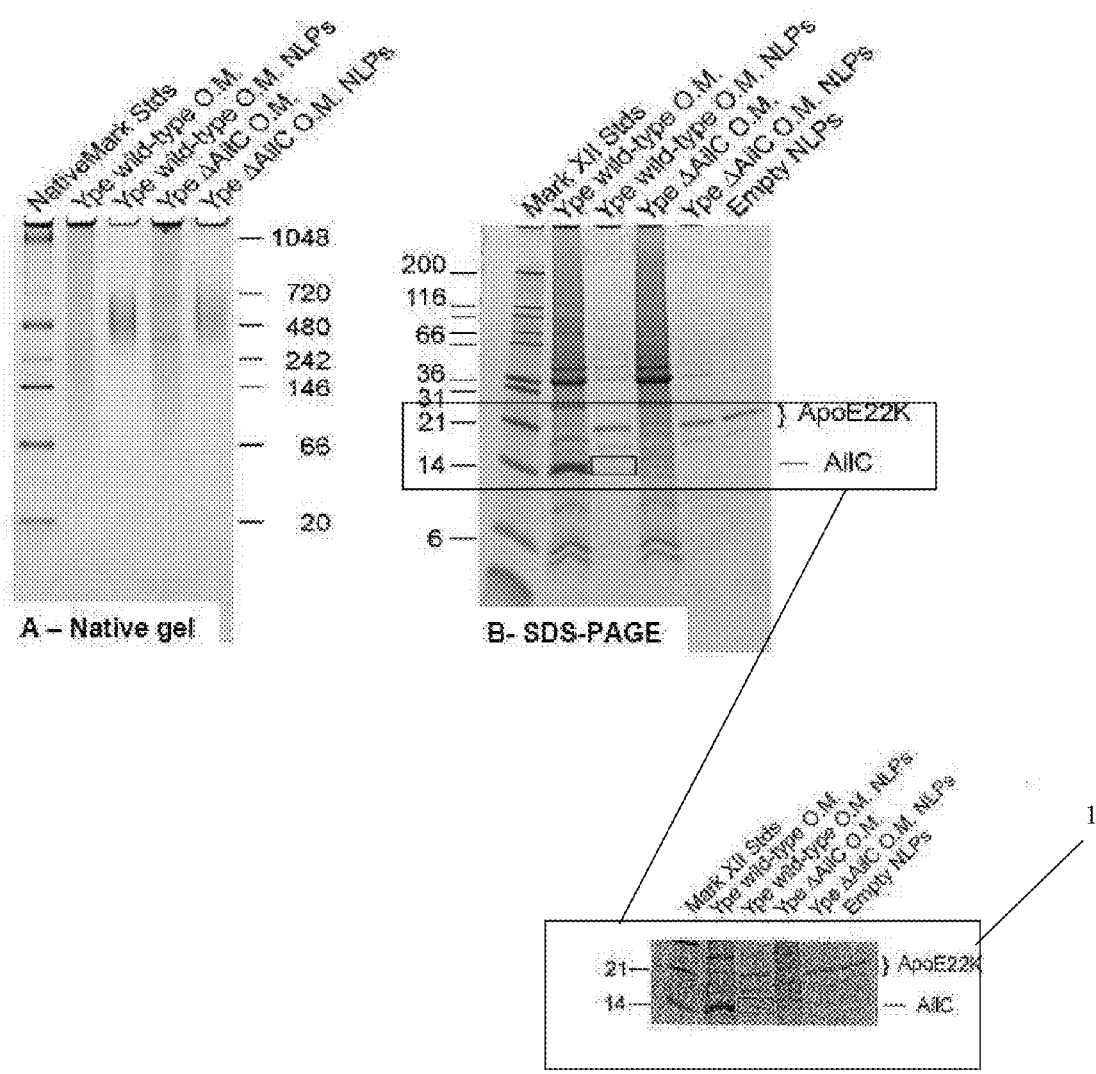
FIG. 8 shows a native gel and an SDS-PAGE gel of MP-NLPs that show the solubilization of AilC, a high abundant membrane protein from the *Y. pestis* outer membrane. Panel A shows a native gel that highlights the solubility of the MP-N The term "assemble" or "assembly" as used herein indicate the fitting together of the components of a molecular structure into said structure. Accordingly, when used with reference to nanolipoproteins, the term "assemble" indicates the fitting together nanolipoprotein components into a nanoliprotein particle.
Figure 9:
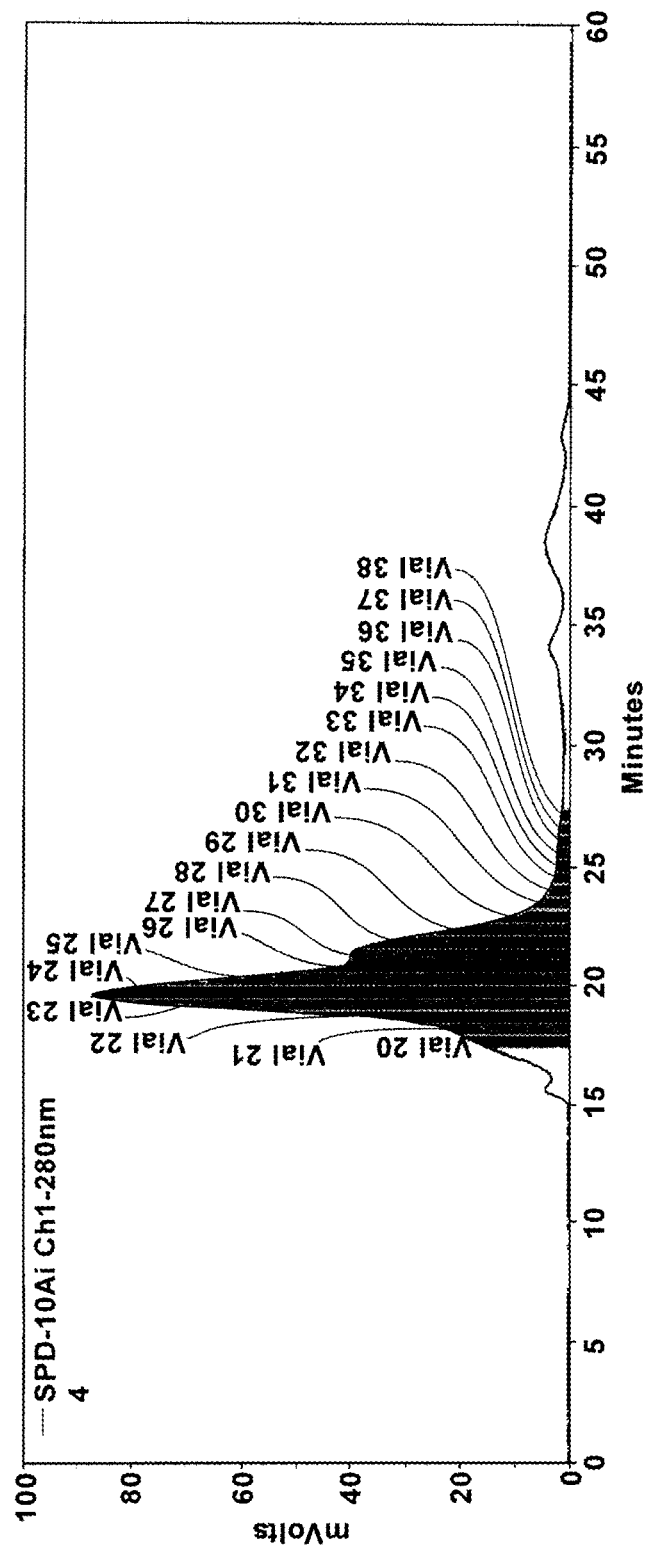
Figure 10:
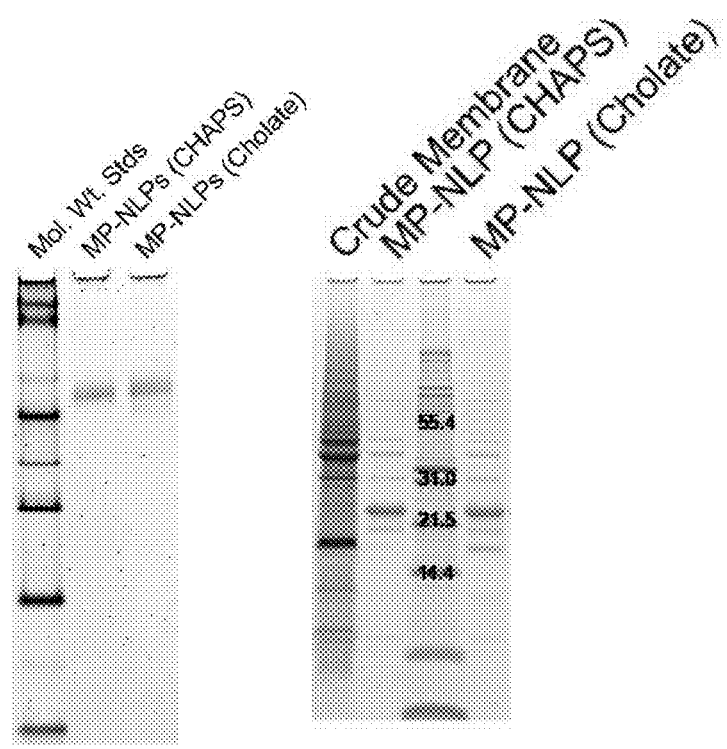
Figure 11A:
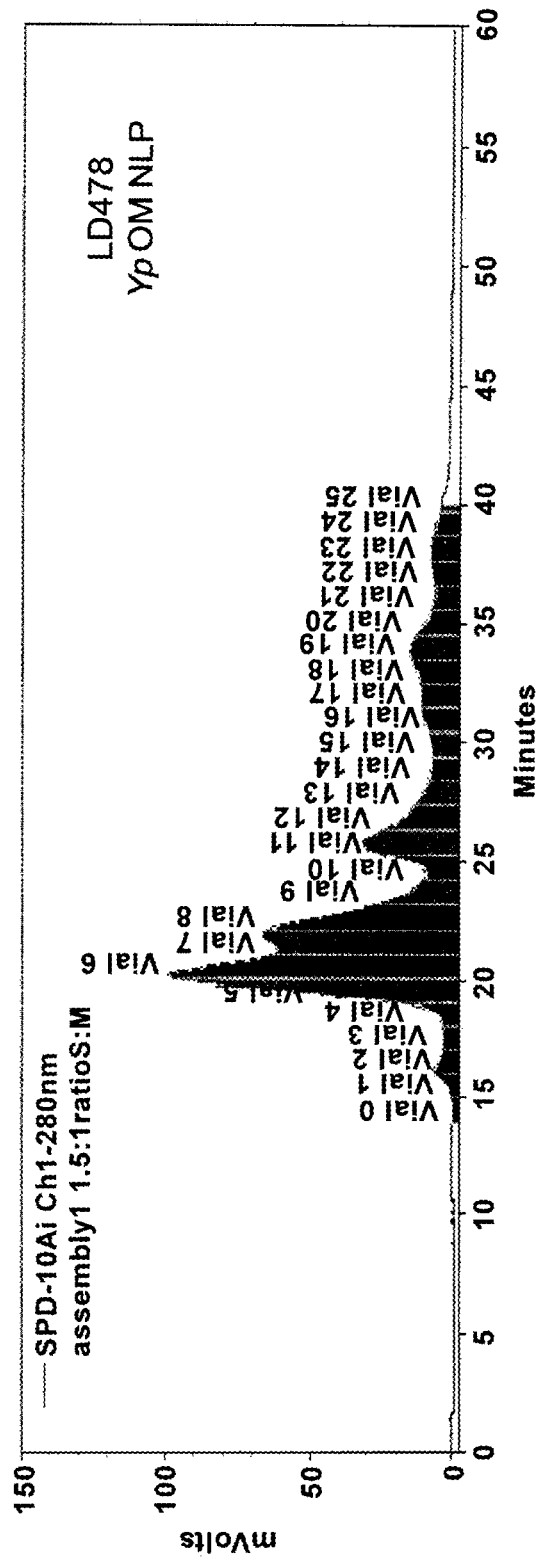
Figure 11B:
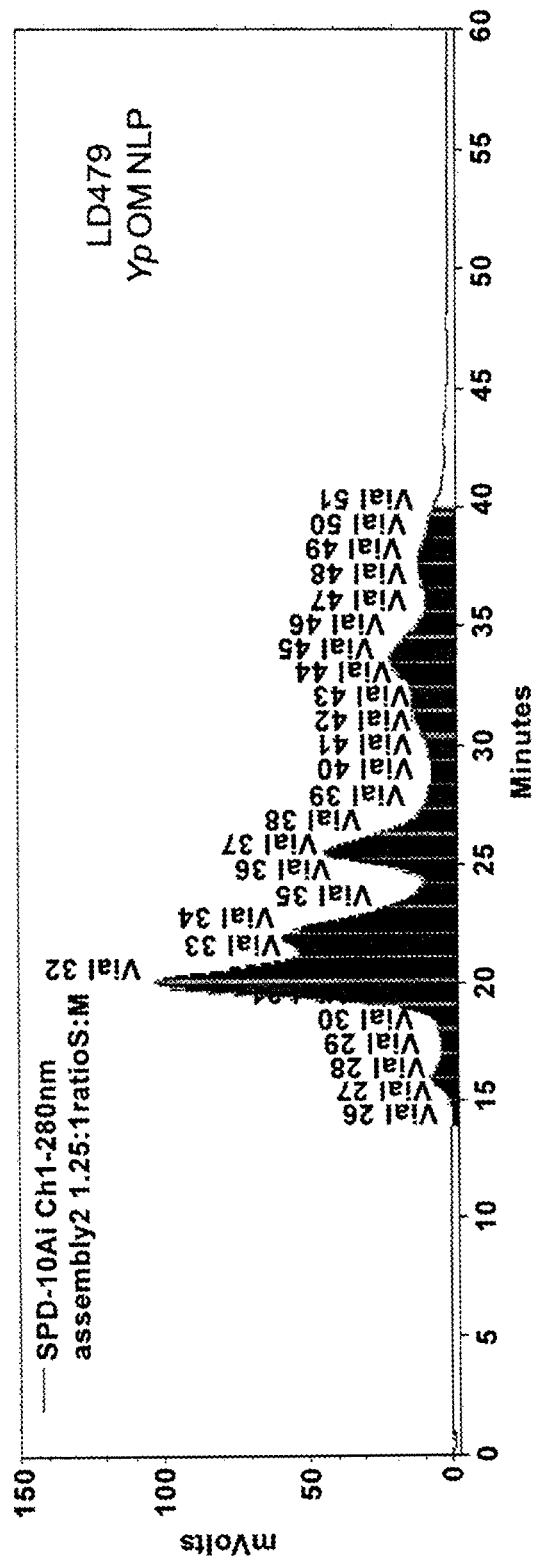
Figure 11C:
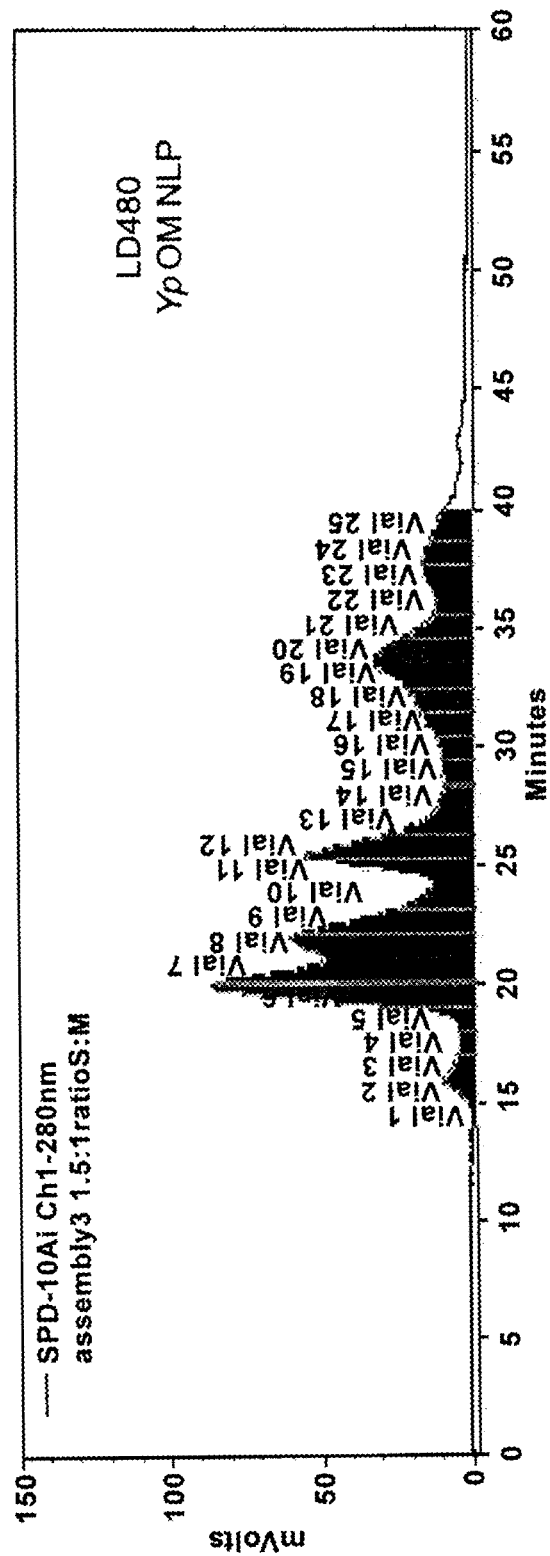
Figure 11D:
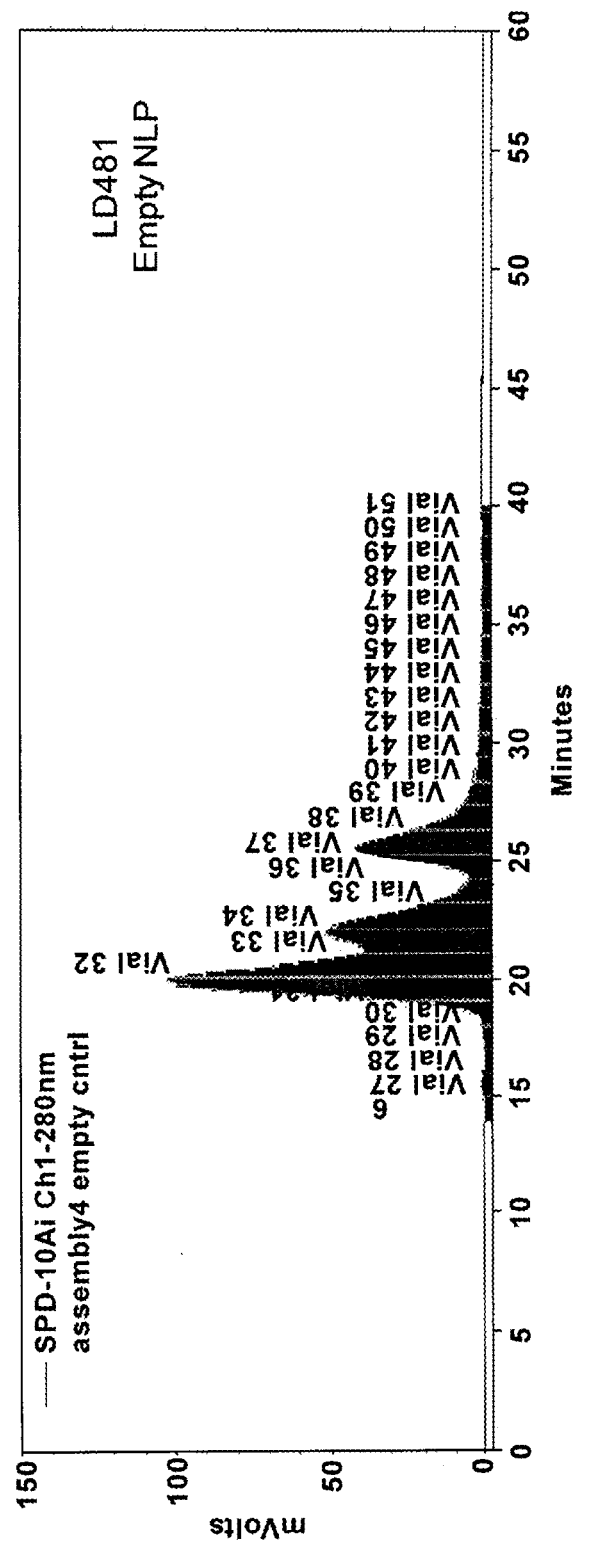
Figure 12:
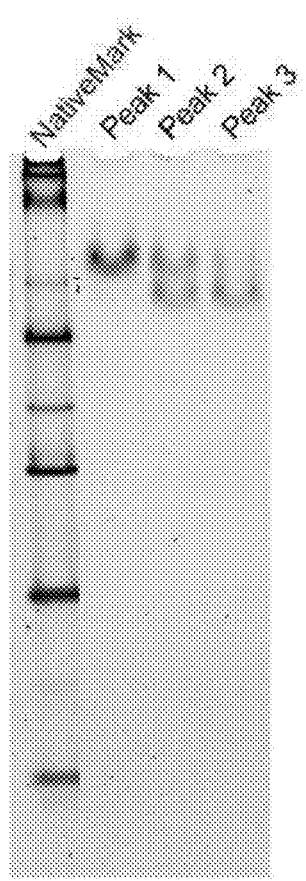
Figure 13:
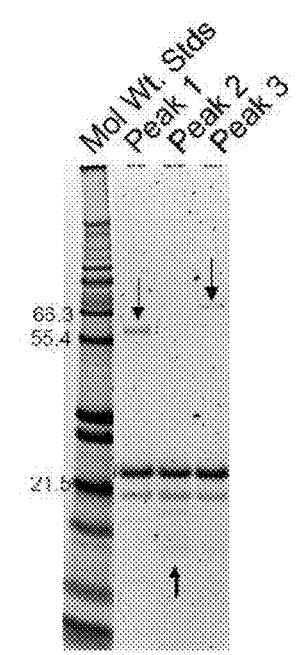

The results illustrated in the SDS-PAGE of FIG. 8 indicate that the outer membranes from two different *Y. pestis* strains can be incorporated into NLPs. These results highlight the ability of this process to incorporate high abundant membrane proteins from particular membrane preparations. Importantly, the two strains differ only in the presence or absence of a particular high abundant outer membrane protein, called AilC. The AilC band on the SDS-PAGE is clearly evident in the highlighted box. The AilC knockout strain (ΔAilC) shows no AilC protein in the NLPs. All samples, empty NLPs, AilC knockout membrane-NLPs, and wild-type AilC-NLPs, all show the apoE422k apolipoprotein. The method used for these assemblies is shown in FIGS. 1A-1B.

Example 5

Different Detergent Tested for the Formation of NLPs

Membrane preparations from various sources can also be sequestered into NLPs using both methods shown in FIGS. 5 and 10 using detergents other than cholate. FIGS. 4A-4F show five different detergents that can be used to form NLPs. These include Pentaethylene glycol monodecylether, DDM, Chaps, Dimethlydodecylammonio propanesulfonate, and O-n-Decylphophorylcholine. FIGS. 4A-4F show the SEC purified peak of NLPs and the native gel characterization showing the molecular weight and purity of the NLPs made with other detergents are all similar. FIG. 10 shows the native page gel (panel A) and the SDS-PAGE (panel B) of *Y. pestis* membrane proteins incorporated into NLPs (MP-NLPs) using both CHAPs and cholate according to the methods established in FIG. 2.

Example 6

In Situ Vs. Detergent Dialysis

Membrane preparations from *Y. pestis* were prepared using two different methods, namely in situ vs. detergent dialysis.

Example 7

Incorporation of Inner Membrane Preparations from *Acinetobacter Baumannii* in NLPs Membrane preparations from A. *Baumannii* were prepared using the inner membrane solubilization technique contained in this application, which is contained within the outer membrane technique. The results of incorporation are shown in FIGS. 20 to 23. FIG. 20 shows the size exclusion chromatography of multiple sized MP-NLPs using different ratios of membrane proteins relative to the apoE22k scaffold protein. The protocol followed was as shown in FIG. 2. FIG. 21 shows the membrane proteins that have been incorporated into NLPs by SDS-PAGE. Bands on the gel either correspond to the scaffold protein or to proteins that were solubilized from inner membranes into NLPs.

Example 8

NLPs Protein Capture of Hydrogenase from Crude Membrane Preparation

Proteins were captured in NLPs from crude membrane preparations according to an approach illustrated in the schematic representation of FIG. 1B.

In particular, total cell membranes were homogenized in 1 ml of homogenization buffer (10 mM Tris-HCI, pH 7.4, 1 mM EDTA, 200 mM sucrose, 1 mM phenylmethylsulfonyl fluoride, PMSF).—Nuclei and cell debris were removed from the homogenate by centrifugation at 900×g for 10 min at 4° C. The supernatant was centrifuged at 110,000×g for 75 min at 4° C. (SW40 rotor, Beckman ultracentrifuge) and the membrane pellet solubilized in buffer (10 mM Tris-HCl, pH 7.4, 1 mM EDTA, 0.5% Triton X-100, 1 mM PMSF) for a minimum of 1 h at 4° C. The insoluble material was then removed by centrifugation at 14,000×g for 10 min at 4° C. and 1 ug/ml aprotinin added to solubilized membrane samples prior to storage at 70° C.

The NLP so formed was used to analyze properties and functions of membrane proteins of interest. In particular, an in vitro H2 production from cellulosic Biomass and NLP-Hydrogenase membrane was performed according to the approach illustrated in the schematic representation of FIG. 1B following the teaching of Woodward et al (1996) Nature Biotech 14:872-876 herein incorporated by reference in its entirety.

Example 9

Monitoring Formation and Characterization of an NLP Particle Assembled Using Methods and Systems Herein Disclosed Assembly of NLPs formed with the method and system illustrated in Example 2, was monitored using several techniques. In a first series of experiments, a specific fluorescent labeling was used to follow NLP formation according to an original approach illustrated in FIG. 7.

FIG. 7 shows the schematic of how fluorescently labeled MP-NLPs can be made. The technique is identical to the in situ formation shown in FIG. 2, except that fluorescent lipid and protein are implemented to better detect the formation of MP-NLPs. FIG. 7 shows the resulting MP-NLPs using the fluorescent tagged detection strategy by native and denatured gels. This figure also shows that in situ and ex situ techniques are both successful at assembling, solubilizing, and purifying membrane proteins from crude membrane preparations.

The inclusion and proper folding of a protein of interest into the NLP formed using the methods and systems herein disclosed was also verified by way of the methods and systems for monitoring production of a target protein in a nanolipoprotein particle described in U.S. patent application Ser. No. 12/118,530 herein incorporated by reference in its entirety.

Properly folded Bacterial Opsin (bOp) binds retinal (Ret) to give bacteriorhodopsin (bR) and turns purple. Both Invitrogen (IVGN) Expressway and Roche RTS reactions express active bOp in the presence of nanolipoprotein particles (NLPs) that binds Ret to produce functionally active bR.

Example 10

Characterization of Hydrogenase NLPs

Membrane preparations from *P. furiosus* were obtained as reported in to U.S. application entitled "Nanolipoprotein Particles comprising Functional Membrane Associated Biocatalysts and related Assemblies, Methods and Systems", filed on the same day of the present application.

Example 11

Solubilization of Hydrogenase Complex in NLPs

Figure 20:
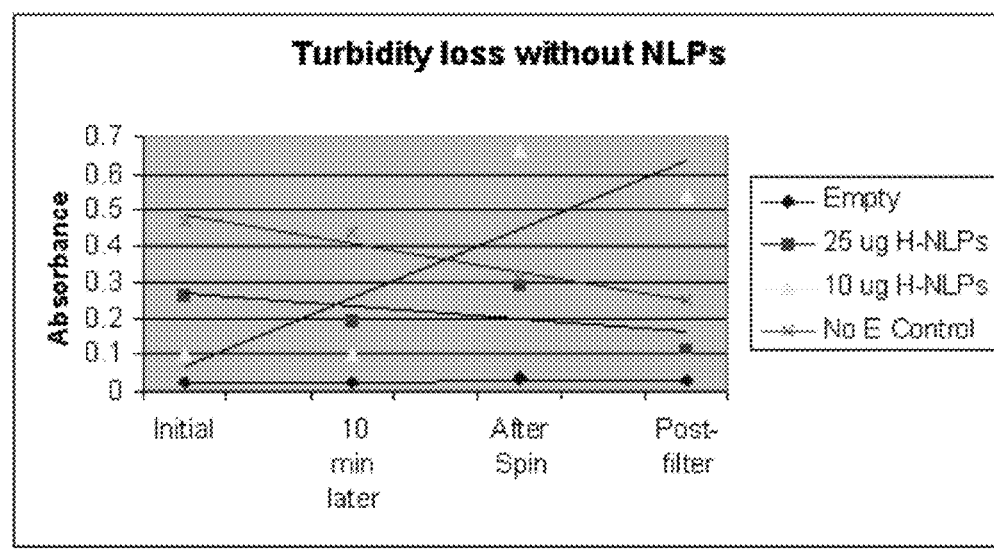
Figure 21:
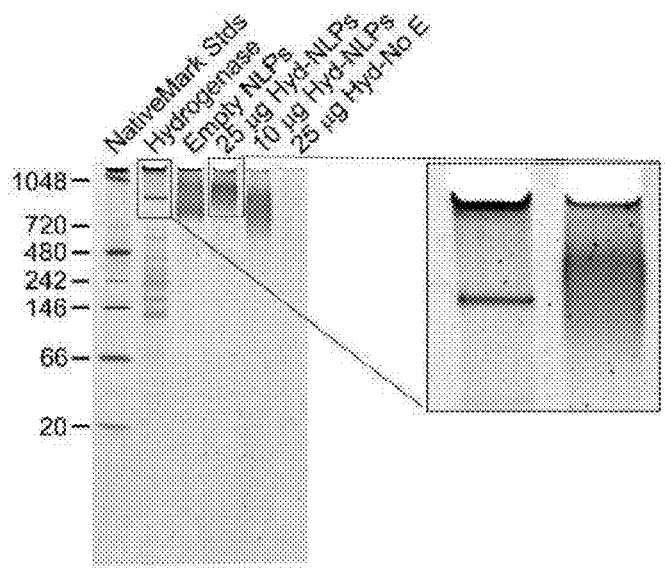
Figure 22:
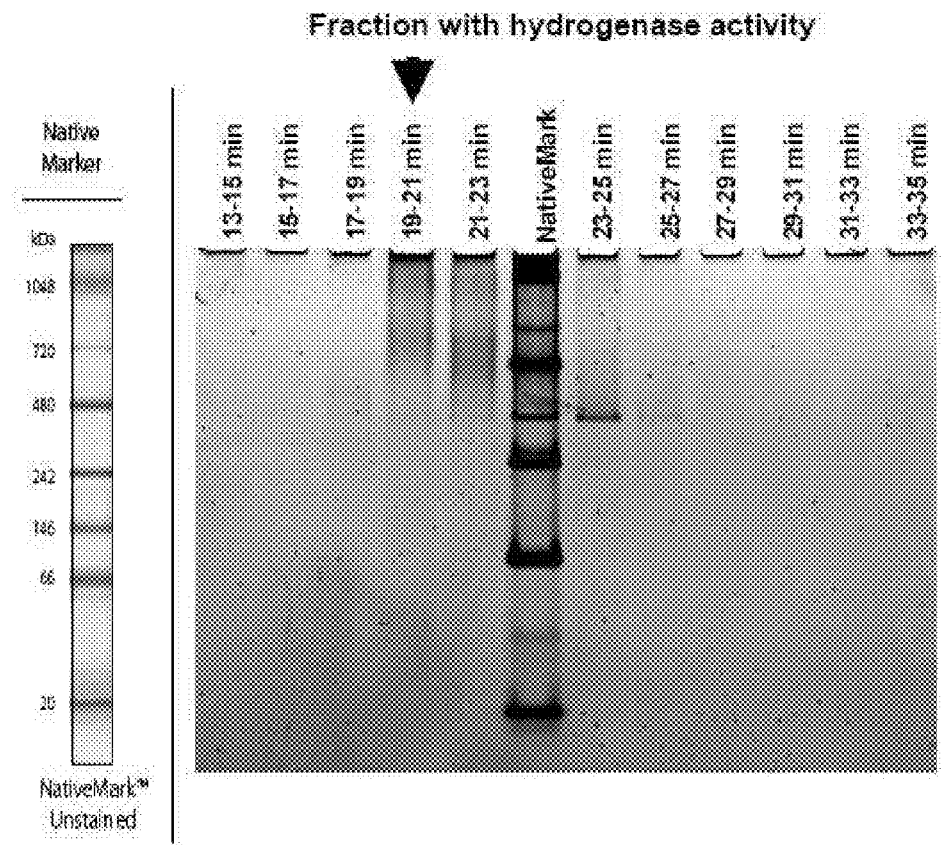
Figure 23:
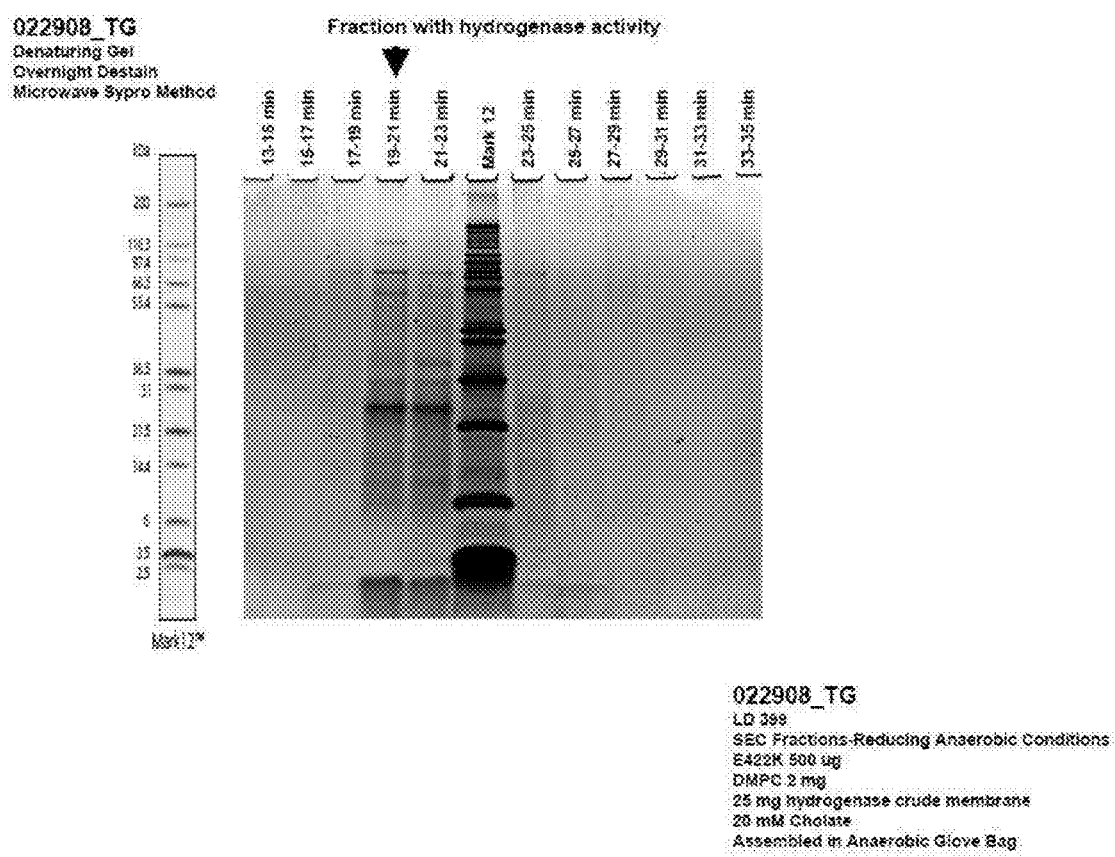

Membrane preparations from *P. furiosus* were incubated using the in situ formation technique and examined for turbidity (FIG. 20). The membranes that were not incubated with NLP components failed to stay in solution, instead quickly settling to the bottom of the tube. MP-NLP formation, however, maintained the hydrogenase membrane complex in solution, therefore, this technology was able to successfully solubilize the complex. FIG. 21 highlights the differences between the hydrogenase membranes that are insoluble and the membrane proteins that become soluble due to the in situ method.

Example 12

Hydrogenase Incorporated in NLPs Maintains Functionality

Figure 24:
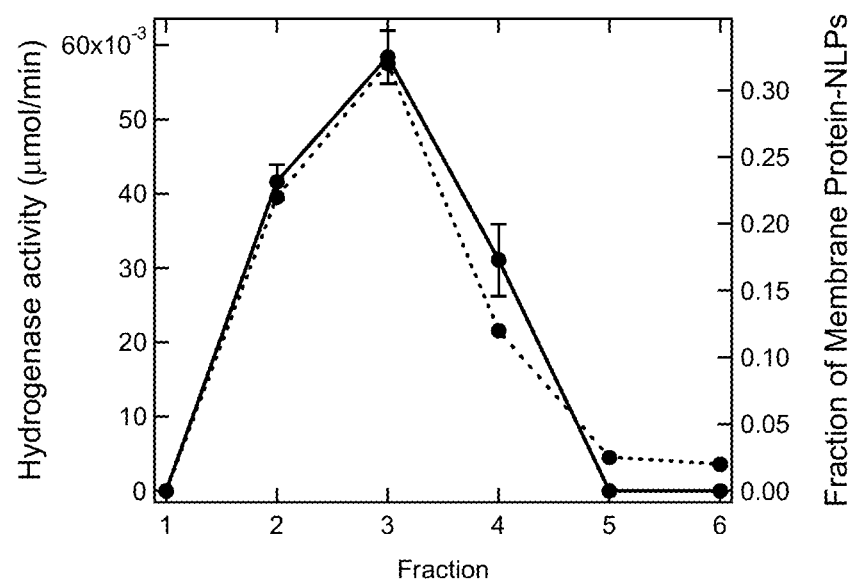
Figure 25:
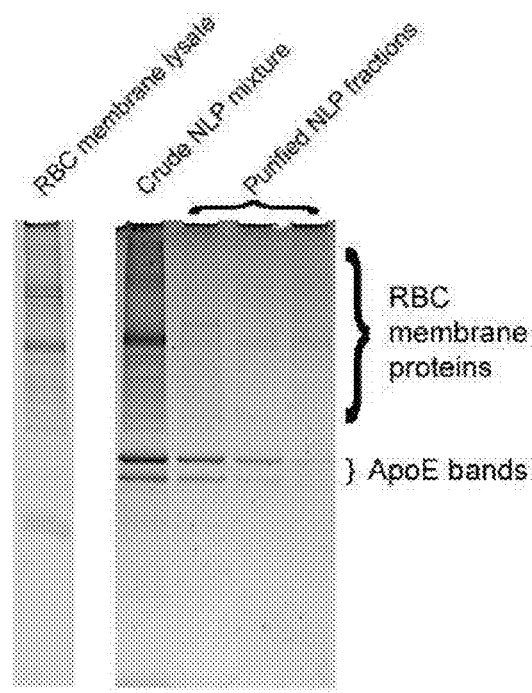

Membrane preparations from *P. furiosus* Cellular membranes from pfu lysates were separated from cellular debris and washed using centrifugation as previously described (Sapra 2000). A suspension of the membranes in TBS was added to a mixture of DMPC, apoE22k, and cholate (20 mM). The mixture was briefly vortexed and temperature cycled starting at 30° C. for ten minutes followed by 20° C. for ten minutes. This cycle was repeated two more times (3 times total). Following cycling, the mixture was incubated at 23.8° C. overnight. Following this overnight incubation at the transition temperature of DMPC, samples were separated by size exclusion chromatography to purify MP-NLPs from lipid-rich and lipid-poor structures. Fractions were then examined for structure by atomic force microscopy and tested for molecular weight and purity by native and SDS-PAGE. NLPs were tested for functional hydrogen production using and established gas chromatography assay (Sapra 2003). FIG. 24 shows the hydrogenase activity of the different NLP fractions. This result shows that the incorporated hydrogenase.

Example 13

Red Blood Cells (RBC) Membrane in NLPs

RBC membrane preparations were incorporated into NLPs and the more abundant RBC membrane proteins were successfully captured in NLPs. RBC membranes were made essentially as described (Pasini E M et al, 2006). Packed RBCs (10 mL) were suspended in 50 mL ice-cold 5 mM phosphate buffer, pH 8, and centrifuged (9000 g, 20 minutes, 4° C.). Hemolysate was discarded and the operation repeated (at least 5 times) until the supernatant appeared colorless. Centrifugation was then increased to 20 000 g and washing was repeated until the ghost membranes appeared yellow-whitish. Membranes were stored at −80° C. These crude RBC membranes were then added to apoE22k and DMPC in a ratio of (8:2:1) (DMPC:E422k:RBC membrane) in the presence of 20 mM cholate. The complex was vortexed, placed in temperature transition three times starting at 30° C. and then 20° C. Following transition, the sample was incubated o/n at the transition temperature of DMPC (23.8° C.).

Example 14

Solubilization of a Membrane Protein

Harvest total cell membranes from bacteria or other cells (yeast, mammalian cells, etc.) by high speed centrifugation (~100k×g) following lysis and low speed centrifugation (~16k×g). The lysis can be accomplished with sonication, rapid shaking with small glass or zirconium beads (bead beating), or chemical shearing. Pressure lysis can also generate appropriate lysis of cells to enable crude membrane capture. An example of this solubilization is shown in Blanchette et al., 2008.

Example 15

Purification of a Membrane Protein

In an exemplary procedure, starting from crude, or semi-purified cell membrane fractions, Applicants added them to a tube containing phospholipid (PL), purified apolipoprotein, a detergent surfactant, e.g. cholate in a solution of TBS. The mixture is subjected to a temperature cycle step based on the gel to liquid/crystalline transition temperature for the phospholipid and then incubated for 20-24 hours at the PL melting temperature (although shorter time for incubation may be sufficient). The detergent is then dialyzed out of the reaction mixture and the subsequent membrane protein containing NLP is separated from the unreacted PL and apolipoprotein by size-exclusion chromatography; the fractions containing NLPs are collected, pooled and concentrated by dialysis. For example, AilC was purified and solubilized from crude *Y. pestis* outer membrane fractions using DMPC, cholate, and apolipoprotein E422K yielding NLPs containing several proteins including the AilC target. Another example is to replace inner membrane proteins from *Acinetobacter baumanii* with everything else being the same.

The examples set forth above are provided to give those of ordinary skill in the art a complete disclosure and description of how to make and use the embodiments of the NLPs, methods and systems of the disclosure, and are not intended to limit the scope of what the inventors regard as their disclosure. Modifications of the above-described modes for carrying out the disclosure that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

The entire disclosure of each document cited (including patents, patent applications, journal articles, abstracts, laboratory manuals, books, or other disclosures) in the Background, Summary, Detailed Description, and Examples is hereby incorporated herein by reference.

It is to be understood that the disclosures are not limited to particular compositions or biological systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

Although any methods and materials similar or equivalent to those described herein can be used in the practice for testing of the specific examples of products, methods and system of the present disclosure, exemplary appropriate materials and methods are described herein.

A number of embodiments of the disclosure have been described. Nevertheless, it will be understood that various modifications may be made without departing from the spirit and scope of the present disclosure. Accordingly, other embodiments are within the scope of the following claims.

REFERENCES

1. Silvius, J. R. (1982) Thermotropic phase transitions of pure lipids in model membranes and their modification by membrane proteins. In Lipid-Protein Interactions (P. C. Jost and O. H. Griffith, Eds.) Vol. 2. New York: Wiley.
2. Cullis P R and Hope M J (1991) Physical properties and functional roles of lipids in membranes. In Biochemistry of Lipids, Lipoproteins, and Membranes (D. E. Vance and J. Vance, Eds.). Vol. 20. New York: Elsevier.
3. North P. and Fleischer S. (1983) *J. Biol. Chem.* Vol. 258, No. 2. pp. 1242-1253
4. Bockaert J., Brand C., Journot, L. (1997), Do Recombinant Receptor Assays Provide Affinity and Potency. In Receptor Classification: The integration of operational, structural, and transductional information (D. G. Trist, P. P. A. Humphrey, P. Leff, and N. P. Shankley, Eds.). Vol. 812. New York, N. Y. Academy of Sciences.
5. Tufteland M Peptides (2007) 28:741-748
6. Jonas, A. Methods Enzymol. 1986, 128, 553-82
7. Bayburt, T. H.; Grinkova, Y. V.; Sligar, S. G. Nano Lett. 2002, 2, 853-856
8. Chromy et al., 2007, Different Apolipoproteins Impact Nanolipoprotein Particle Formation. J. Amer Chem. Soc. 129, 14348-14354
9. J. Wang, S. Link, C. D. Heyes and M. A. El-Sayed, Comparison of the dynamics of the primary events of bacteriorhodopsin in its trimeric and monomeric states, Biophys. J. 83 (2002), pp. 1557-1566
10. G. Bacher, R. Korner, A. Atrih, S. J. Foster, P. Roepstorff and G. Allmaier, Negative and positive ion matrix-assisted laser desorption/ionization time-of-flight mass spectrometry and positive ion nano-electrospray ionization quadrupole ion trap mass spectrometry of peptidoglycan fragments isolated from various *bacillus* species, J. Mass Spectrom. 36 (2001), pp. 124-139
11. Woodward et al (1996) Nature Biotech 14:872-876
12. Sapra R et al, J Bacteriol. 2000 182, (12) 3423-3428.
13. Sapra R et al., J Bacteriol 2003, 100 (13), 7545-7550
14. Pasini E M et al., 2006 Blood, 108: 791-801
15. Blanchette et al., accepted (BBA membranes) Biochim Biophys Acta. 2008, Dec. 8. [Epub ahead of print] Atomic force microscopy differentiates discrete size distributions between membrane protein containing and empty nanolipoprotein particles.

What is claimed is:

1. A method for solubilizing a membrane associated protein from a cell membrane, the method comprising
    contacting the cell membrane with a scaffold protein and a membrane forming lipid to provide an admixture, the membrane forming lipid having a membrane forming lipid gel-crystalline transition temperature; and
    subjecting the admixture to at least three temperature transition cycles in presence of a detergent, for a time and under condition to allow assembly of a nanolipoprotein particle comprising a solubilized target protein, the temperature transition cycle comprising:
    a temperature increase step wherein the admixture is brought to a temperature above said membrane forming lipid gel crystalline transition temperature and
    a temperature decrease step wherein the admixture is brought to a temperature below said membrane forming lipid gel crystalline transition temperature.

2. The method of claim 1, wherein the cell membrane contacted with the membrane forming lipid and the scaffold protein, is in a crude cell pellet or a membrane fraction.

3. The method of claim 1, wherein the cell membrane is an inner membrane of gram-negative bacteria, an outer membrane of gram-negative bacteria, a single bilayer membrane of gram-positive bacteria, or a plasma membrane of a eukaryotic cell.

4. The method of claim 1, further comprising incubating the admixture subjected to the temperature transition cycle at the membrane forming lipid gel-crystalline transition temperature for a predetermined amount of time that is functional to a desired amount of assembled nanolipoprotein particles.

5. The method of claim 1, further comprising removing the detergent from the admixture subjected to the temperature transition cycle.

6. The method of claim 1, wherein the membrane forming lipid is contacted with the membrane associated protein and the scaffold protein at a temperature above the membrane forming lipid gel-crystalline transition temperature.

7. The method of claim 1, wherein subjecting the admixture to a temperature transition cycle in presence of a detergent is performed by subjecting the admixture to multiple temperature transition cycles.

8. The method of claim 1, wherein the temperature increase step and/or the temperature decrease step are performed for a time and under conditions such that at least a fraction of the membrane forming lipid molecules in the admixture changes state.

9. The method of claim 1, wherein the membrane associated protein contacted with the membrane forming lipid and with the scaffold protein is comprised in a cell membrane.

* * * * *

UNITED STATES PATENT AND TRADEMARK OFFICE
CERTIFICATE OF CORRECTION

PATENT NO. : 9,458,191 B2
APPLICATION NO. : 14/536513
DATED : October 4, 2016
INVENTOR(S) : Brett A. Chromy et al.

Page 1 of 1

It is certified that error appears in the above-identified patent and that said Letters Patent is hereby corrected as shown below:

In the Specification

In the body of the text, under the title "STATEMENT OF GOVERNMENT GRANT", Column 1, Lines 37-40, delete the paragraph "The United States Government has rights in this invention pursuant to Contract No. DE-AC52-07NA27344 between the U.S. Department of Energy and Lawrence Livermore National Security, LLC." and replace with the paragraph "The United States Government has rights in this invention pursuant to Contract No. DE-AC52-07NA27344 between the United States Department of Energy and Lawrence Livermore National Security, LLC, for the operation of Lawrence Livermore National Laboratory."

Signed and Sealed this
Nineteenth Day of February, 2019

Andrei Iancu
*Director of the United States Patent and Trademark Office*